(12) United States Patent
Tanaka et al.

(10) Patent No.: US 7,049,490 B2
(45) Date of Patent: May 23, 2006

(54) GIBBERELLIN 3β-HYDROXYLASE GENES OF RICE AND USES THEREOF

(75) Inventors: Hiroshi Tanaka, Tsukuba (JP);
Toshiaki Kayano, Tsukuba (JP);
Masahiro Yano, Tsukuba (JP); Makoto Matsuoka, Nagoya (JP); Masatomo Kobayashi, Tsukuba (JP)

(73) Assignees: National Institute of Agrobiological Sciences, Tsukuba (JP); Riken, Wako (JP)

( * ) Notice: Subject to any disclaimer, the term of this patent is extended or adjusted under 35 U.S.C. 154(b) by 290 days.

(21) Appl. No.: 10/168,780

(22) PCT Filed: Dec. 20, 2000

(86) PCT No.: PCT/JP00/09037

§ 371 (c)(1),
(2), (4) Date: Nov. 5, 2002

(87) PCT Pub. No.: WO01/46434

PCT Pub. Date: Jun. 28, 2001

(65) Prior Publication Data

US 2003/0172405 A1    Sep. 11, 2003

(30) Foreign Application Priority Data

Dec. 20, 1999    (JP) .................... 11-361608

(51) Int. Cl.
*C12N 15/29* (2006.01)
*C12N 15/82* (2006.01)
*C12N 5/04* (2006.01)
*C12N 15/55* (2006.01)
*A01H 5/00* (2006.01)

(52) U.S. Cl. .................... 800/298; 536/23.2; 536/23.6; 435/320.1; 435/419; 435/195; 800/278

(58) Field of Classification Search ............... 536/23.1, 536/23.6; 435/468, 419, 320.1, 195; 800/298, 800/278, 290
See application file for complete search history.

(56) References Cited

U.S. PATENT DOCUMENTS 5,925,807 A * 7/1999 Chiang et al. .............. 800/298
5,939,539 A * 8/1999 Lange et al. ................ 536/23.2

FOREIGN PATENT DOCUMENTS

WO    WO 98/59057 A1    12/1998
WO    WO 01/48215 A1    7/2001

OTHER PUBLICATIONS

Martin, D.N. et al. "Mendel's dwarfing gene: cDNAs from the *Le* alleles and function of expressed proteins" *Proc. Natl. Acad. Sci. USA* 94:8907-8911 (Aug. 1997).

Chiang, H-H. et al. "Isolation of the arabidopsis GA4 locus" *The Plant Cell* 7:195-201 (Feb. 1995).

Lange, T. et al. "Expression cloning of a gibberellin 20-oxidase, a multifunction exzyme involved in gibberellin biosynthesis" *Proc. Natl. Acad. Sci. USA* 91:8552-8556 (Aug. 1994).

Lester, D.R. et al. "Mendel's stem length gene (*Le*) encodes a gibberellin 3β-hydroxylase" *The Plant Cell* 9:1435-1443 (Aug. 1997).

Itoh, H. et al. "Cloning and functional analysis of two gibberellin 3β-hydroxylase genes that are differently expressed during the growth of rice" *Proc. Natl. Acad. Sci. USA* 98(15):8908-8914 (Jul. 17, 2001).

Lange, T. et al. "Cloning and expression of a gibberellin 2β, 3β-hydroxylase cDNA from pumpkin endosperm" *Plant Cell* 9(8):1459-67 (Aug. 1997).

Sakamoto, T. et al. "Gibberellin seigousei kouso idenshi no hatsugen chousetsu ni yoru ine kusagata no jiniteki seigyo" *Kagaku to Seibutsu* 38(2):131-139 (Feb. 2000).

Hedden, P. et al. "Recent advances in gibberellin biosynthesis" *Journal of Experimental Biology* 50(334):553-563 (May 1999).

Yamaguchi, S. et al. "Gibberellin no seigousei kenkyu; saishin no shinpo(1)" *Kagaku to Seibutsu* 34(6):402-410 (Jun. 1996).

Sakamoto et al. "Artificial regulation of rice plant shape by controlling the expression of gibberellin biosynthetic enzyme gene" *Kagaku to Seibutsu* 38(2):131-139 (2000).

Yamaguchi et al. "Recent progess in studies of gibberellin biosynthesis" *Kagaku to Seibutsu* 34(6):402-410 (1996).

Honda, Ichiro, et al., "Characterization of Endogenous Gibberellins in Dwarf Rice Mutants," *Biosci. Biotech. Biochem.*, vol. 60(12):2073-2075 (1996).

\* cited by examiner

*Primary Examiner*—David T. Fox
*Assistant Examiner*—Stuart F. Baum
(74) *Attorney, Agent, or Firm*—Lahive & Cockfield, LLP; Elizabeth A. Hanley, Esq.; Jeanne M. DiGiorgio, Esq.

(57) ABSTRACT

Genomic DNA and cDNA encoding GA 3β-hydroxylase were isolated from rice. When the expression of these genes was suppressed in rice plants, the plants became dwarfed compared with the wild type plants.

5 Claims, 10 Drawing Sheets a b

T-65　　Kotake-tamanishiki d18k　　Waito-C d18-w　　Hosetsu-waisei d18-h

Akibare-waisei d18-AD control (Nipponbare)    transgenic recombinant with antisense 3β-hydroxylase gene

SEQUENCE LISTING

```
<160> NUMBER OF SEQ ID NOS: 8

<210> SEQ ID NO 1
<211> LENGTH: 379
<212> TYPE: PRT
<213> ORGANISM: Oryza sativa
```

```
<400> SEQUENCE: 1

Met Thr Ser Ser Thr Ser Pro Thr Ser Pro Leu Ala Ala Ala
 1               5                  10                  15

His Asn Gly Val Thr Ala Ala Tyr Phe Asn Phe Arg Gly Ala Glu Arg
             20                  25                  30

Val Pro Glu Ser His Val Trp Lys Gly Met His Glu Lys Asp Thr Ala
         35                  40                  45

Pro Val Ala Ala Asp Ala Asp Gly Gly Asp Ala Val Pro Val Val
     50                  55                  60

Asp Met Ser Gly Gly Asp Asp Ala Ala Val Ala Val Ala Arg Ala
 65                  70                  75                  80

Ala Glu Glu Trp Gly Gly Phe Leu Leu Val Gly His Gly Val Thr Ala
                 85                  90                  95

Glu Ala Leu Ala Arg Val Glu Ala Gln Ala Ala Arg Leu Phe Ala Leu
             100                 105                 110

Pro Ala Asp Asp Lys Ala Arg Gly Ala Arg Arg Pro Gly Gly Gly Asn
             115                 120                 125

Thr Gly Tyr Gly Val Pro Pro Tyr Leu Leu Arg Tyr Pro Lys Gln Met
130                 135                 140

Trp Ala Glu Gly Tyr Thr Phe Pro Pro Ala Ile Arg Asp Glu Phe
145                 150                 155                 160

Arg Arg Val Trp Pro Asp Ala Gly Asp Asp Tyr His Arg Phe Cys Ser
                 165                 170                 175

Ala Met Glu Glu Tyr Asp Ser Ser Met Arg Ala Leu Gly Glu Arg Leu
             180                 185                 190

Leu Ala Met Phe Phe Lys Ala Leu Gly Leu Ala Gly Asn Asp Ala Pro
         195                 200                 205

Gly Gly Glu Thr Glu Arg Lys Ile Arg Glu Thr Leu Thr Ser Ser Thr
     210                 215                 220

Ile His Leu Asn Met Phe Pro Arg Cys Pro Asp Pro Asp Arg Val Val
225                 230                 235                 240

Gly Leu Ala Ala His Thr Asp Ser Gly Phe Phe Thr Phe Ile Leu Gln
                 245                 250                 255

Ser Pro Val Pro Gly Leu Gln Leu Leu Arg His Arg Pro Asp Arg Trp
             260                 265                 270

Val Thr Val Pro Gly Thr Pro Gly Ala Leu Ile Val Val Gly Asp
         275                 280                 285

Leu Phe His Val Leu Thr Asn Gly Arg Phe His Ser Val Phe His Arg
290                 295                 300

Ala Val Val Asn Arg Glu Arg Asp Arg Ile Ser Met Pro Tyr Phe Leu
305                 310                 315                 320

Gly Pro Pro Ala Asp Met Lys Val Thr Pro Leu Val Ala Ala Gly Ser
                 325                 330                 335

Pro Glu Ser Lys Ala Val Tyr Gln Ala Val Thr Trp Pro Glu Tyr Met
             340                 345                 350

Ala Val Arg Asp Lys Leu Phe Gly Thr Asn Ile Ser Ala Leu Ser Met
         355                 360                 365

Ile Arg Val Ala Lys Glu Glu Asp Lys Glu Ser
370                 375

<210> SEQ ID NO 2
<211> LENGTH: 373
<212> TYPE: PRT
<213> ORGANISM: Oryza sativa
```

```
<400> SEQUENCE: 2

Met Pro Thr Pro Ser His Leu Lys Asn Pro Leu Cys Phe Asp Phe Arg
 1               5                  10                  15

Ala Ala Arg Arg Val Pro Glu Thr His Ala Trp Pro Gly Leu Asp Asp
             20                  25                  30

His Pro Val Val Asp Gly Gly Gly Gly Gly Glu Asp Ala Val Pro
         35                  40                  45

Val Val Asp Val Arg Ala Gly Asp Ala Ala Arg Val Ala Arg Ala
     50                  55                  60

Ala Glu Gln Trp Gly Ala Phe Leu Leu Val Gly His Gly Val Pro Ala
 65                  70                  75                  80

Ala Leu Leu Ser Arg Val Glu Glu Arg Val Ala Arg Val Phe Ser Leu
                 85                  90                  95

Pro Ala Ser Glu Lys Met Arg Ala Val Arg Gly Pro Gly Glu Pro Cys
                100                 105                 110

Gly Tyr Gly Ser Pro Pro Ile Ser Ser Phe Phe Ser Lys Leu Met Trp
            115                 120                 125

Ser Glu Gly Tyr Thr Phe Ser Pro Ser Ser Leu Arg Ser Glu Leu Arg
130                 135                 140

Arg Leu Trp Pro Lys Ser Gly Asp Asp Tyr Leu Leu Phe Cys Asp Val
145                 150                 155                 160

Met Glu Glu Phe His Lys Glu Met Arg Arg Leu Ala Asp Glu Leu Leu
                165                 170                 175

Arg Leu Phe Leu Arg Ala Leu Gly Leu Thr Gly Glu Glu Val Ala Gly
            180                 185                 190

Val Glu Ala Glu Arg Arg Ile Gly Glu Arg Met Thr Ala Thr Val His
            195                 200                 205

Leu Asn Trp Tyr Pro Arg Cys Pro Glu Pro Arg Arg Ala Leu Gly Leu
210                 215                 220

Ile Ala His Thr Asp Ser Gly Phe Phe Thr Phe Val Leu Gln Ser Leu
225                 230                 235                 240

Val Pro Gly Leu Gln Leu Phe Arg Arg Gly Pro Asp Arg Trp Val Ala
                245                 250                 255

Val Pro Ala Val Ala Gly Ala Phe Val Val Asn Val Gly Asp Leu Phe
            260                 265                 270

His Ile Leu Thr Asn Gly Arg Phe His Ser Val Tyr His Arg Ala Val
            275                 280                 285

Val Asn Arg Asp Arg Asp Arg Val Ser Leu Gly Tyr Phe Leu Gly Pro
            290                 295                 300

Pro Pro Asp Ala Glu Val Ala Pro Leu Pro Glu Ala Val Pro Ala Gly
305                 310                 315                 320

Arg Ser Pro Ala Tyr Arg Ala Val Thr Trp Pro Glu Tyr Met Ala Val
                325                 330                 335

Arg Lys Lys Ala Phe Ala Thr Gly Gly Ser Ala Leu Lys Met Val Ser
            340                 345                 350

Thr Asp Ala Ala Ala Ala Asp Glu His Asp Asp Val Ala Ala Ala
            355                 360                 365

Ala Asp Val His Ala
    370

<210> SEQ ID NO 3
<211> LENGTH: 1187
<212> TYPE: DNA
<213> ORGANISM: Oryza sativa
```

```
<220> FEATURE:
<221> NAME/KEY: CDS
<222> LOCATION: (1)..(1137)

<400> SEQUENCE: 3 atg aca tcg tcg tcg acc tcg ccg acc tcg ccg ctg gcc gcc gcc gca         48
Met Thr Ser Ser Ser Thr Ser Pro Thr Ser Pro Leu Ala Ala Ala Ala
 1               5                  10                  15 cac aat ggc gtc acc gcc gcc tac ttc aac ttc cgc ggg gcg gag cgc         96
His Asn Gly Val Thr Ala Ala Tyr Phe Asn Phe Arg Gly Ala Glu Arg
             20                  25                  30 gtg ccg gag tcg cac gtg tgg aag ggg atg cac gag aag gac acc gcg        144
Val Pro Glu Ser His Val Trp Lys Gly Met His Glu Lys Asp Thr Ala
         35                  40                  45 ccg gtg gcg gcg gcg gac gcg gac ggc ggc gac gcg gtg ccg gtg gtg        192
Pro Val Ala Ala Ala Asp Ala Asp Gly Gly Asp Ala Val Pro Val Val
     50                  55                  60 gac atg agc ggc ggc gac gac gcc gcg gtg gcg gcg gtg gcg cgc gcg        240
Asp Met Ser Gly Gly Asp Asp Ala Ala Val Ala Ala Val Ala Arg Ala
 65                  70                  75                  80 gcg gag gag tgg ggc ggg ttc ctg ctc gtc ggg cac ggc gtg acc gcg        288
Ala Glu Glu Trp Gly Gly Phe Leu Leu Val Gly His Gly Val Thr Ala
                 85                  90                  95 gag gcc ctg gcg cgc gtc gag gcg cag gcg gcg cgg ctg ttc gcg ctg        336
Glu Ala Leu Ala Arg Val Glu Ala Gln Ala Ala Arg Leu Phe Ala Leu
            100                 105                 110 ccg gcg gac gac aag gcg cgc ggg gcg cgg cgg ccc ggc ggc ggg aac        384
Pro Ala Asp Asp Lys Ala Arg Gly Ala Arg Arg Pro Gly Gly Gly Asn
        115                 120                 125 acc ggc tac ggc gtg ccg ccg tac ctc ctc cgg tac ccg aag cag atg        432
Thr Gly Tyr Gly Val Pro Pro Tyr Leu Leu Arg Tyr Pro Lys Gln Met
    130                 135                 140 tgg gcc gag ggc tac acc ttc cct ccc cct gcc atc cgc gac gag ttc        480
Trp Ala Glu Gly Tyr Thr Phe Pro Pro Pro Ala Ile Arg Asp Glu Phe
145                 150                 155                 160 cgc cgc gtc tgg ccc gac gcc ggc gac gac tac cac cgc ttc tgc tcc        528
Arg Arg Val Trp Pro Asp Ala Gly Asp Asp Tyr His Arg Phe Cys Ser
                165                 170                 175 gcc atg gag gag tac gac tcg tcg atg aga gct ctg ggc gag agg ctc        576
Ala Met Glu Glu Tyr Asp Ser Ser Met Arg Ala Leu Gly Glu Arg Leu
            180                 185                 190 ctc gcc atg ttc ttc aag gcg ctc ggg ctc gcc ggc aac gat gcc ccc        624
Leu Ala Met Phe Phe Lys Ala Leu Gly Leu Ala Gly Asn Asp Ala Pro
        195                 200                 205 ggc ggc gag acc gag cgg aag atc cgc gaa acg ttg acg tcg tcg acg        672
Gly Gly Glu Thr Glu Arg Lys Ile Arg Glu Thr Leu Thr Ser Ser Thr
    210                 215                 220 att cac ctc aac atg ttc cct agg tgt cca gat cca gac cgg gtg gtc        720
Ile His Leu Asn Met Phe Pro Arg Cys Pro Asp Pro Asp Arg Val Val
225                 230                 235                 240 ggg ctg gcg gcg cac acg gac tca ggc ttc ttc acc ttc atc ctg cag        768
Gly Leu Ala Ala His Thr Asp Ser Gly Phe Phe Thr Phe Ile Leu Gln
                245                 250                 255 agc ccc gtg ccg ggg ttg cag ctg ctc cgc cac cgg ccg gac cgg tgg        816
Ser Pro Val Pro Gly Leu Gln Leu Leu Arg His Arg Pro Asp Arg Trp
            260                 265                 270 gtg acg gtt ccg ggg acg ccg ggg gcg ctc atc gtc gtc gtc ggc gat        864
Val Thr Val Pro Gly Thr Pro Gly Ala Leu Ile Val Val Val Gly Asp
        275                 280                 285
```

```
ctc ttc cat gtg ctc acc aac ggg cgc ttc cac agc gtg ttc cac cgc     912
Leu Phe His Val Leu Thr Asn Gly Arg Phe His Ser Val Phe His Arg
    290                 295                 300 gcc gtc gtg aac cgg gag aga gac cgg atc tcc atg ccc tac ttc ctc     960
Ala Val Val Asn Arg Glu Arg Asp Arg Ile Ser Met Pro Tyr Phe Leu
305                 310                 315                 320 ggt ccg ccg gcc gac atg aag gtg aca cct ctc gtg gcg gcg ggg tcg    1008
Gly Pro Pro Ala Asp Met Lys Val Thr Pro Leu Val Ala Ala Gly Ser
                325                 330                 335 ccg gag agc aag gcc gtg tat cag gcc gtg aca tgg ccg gag tac atg    1056
Pro Glu Ser Lys Ala Val Tyr Gln Ala Val Thr Trp Pro Glu Tyr Met
            340                 345                 350 gct gta agg gat aag ttg ttc ggg aca aat ata tcg gcg ttg agc atg    1104
Ala Val Arg Asp Lys Leu Phe Gly Thr Asn Ile Ser Ala Leu Ser Met
        355                 360                 365 att cga gta gcg aag gaa gag gac aag gag agt tagaactatg gtatgattgc  1157
Ile Arg Val Ala Lys Glu Glu Asp Lys Glu Ser
    370                 375 aattatccat gccagaaaaa aaaaaaaaaa                                   1187

<210> SEQ ID NO 4
<211> LENGTH: 1122
<212> TYPE: DNA
<213> ORGANISM: Oryza sativa
<220> FEATURE:
<221> NAME/KEY: CDS
<222> LOCATION: (1)..(1119)

<400> SEQUENCE: 4 atg ccg acg ccg tcg cac ttg aag aac ccg ctc tgc ttc gac ttc cgg      48
Met Pro Thr Pro Ser His Leu Lys Asn Pro Leu Cys Phe Asp Phe Arg
1               5                   10                  15 gcg gcg agg cgg gtg ccg gag acg cac gcg tgg ccg ggg ctg gac gac      96
Ala Ala Arg Arg Val Pro Glu Thr His Ala Trp Pro Gly Leu Asp Asp
                20                  25                  30 cac ccg gtg gtg gac ggc ggc ggc ggc ggc gag gac gcg gtg ccg          144
His Pro Val Val Asp Gly Gly Gly Gly Gly Glu Asp Ala Val Pro
            35                  40                  45 gtg gtg gac gtc agg gcg ggc gac gcg gcg gcg cgg gtg gcg cgg gcg     192
Val Val Asp Val Arg Ala Gly Asp Ala Ala Ala Arg Val Ala Arg Ala
 50                  55                  60 gcg gag cag tgg ggc gcg ttc ctt ctg gtc ggg cac ggc gtg ccg gcg     240
Ala Glu Gln Trp Gly Ala Phe Leu Leu Val Gly His Gly Val Pro Ala
65                  70                  75                  80 gcg ctg ctg tcg cgc gtc gag gag cgc gtc gcc cgc gtg ttc tcc ctg     288
Ala Leu Leu Ser Arg Val Glu Glu Arg Val Ala Arg Val Phe Ser Leu
                85                  90                  95 ccg gcg tcg gag aag atg cgc gcc gtc cgc ggc ccc ggc gag ccc tgc     336
Pro Ala Ser Glu Lys Met Arg Ala Val Arg Gly Pro Gly Glu Pro Cys
                100                 105                 110 ggc tac ggc tcg ccg ccc atc tcc tcc ttc ttc tcc aag ctc atg tgg     384
Gly Tyr Gly Ser Pro Pro Ile Ser Ser Phe Phe Ser Lys Leu Met Trp
            115                 120                 125 tcc gag ggc tac acc ttc tcc cct tcc tcc ctc cgc tcc gag ctc cgc     432
Ser Glu Gly Tyr Thr Phe Ser Pro Ser Ser Leu Arg Ser Glu Leu Arg
        130                 135                 140 cgc ctc tgg ccc aag tcc ggc gac gac tac ctc ctc ttc tgt gac gtg     480
Arg Leu Trp Pro Lys Ser Gly Asp Asp Tyr Leu Leu Phe Cys Asp Val
145                 150                 155                 160
```

-continued

| | | |
|---|---|---|
| atg gag gag ttt cac aag gag atg cgg cgg cta gcc gac gag ttg ctg<br>Met Glu Glu Phe His Lys Glu Met Arg Arg Leu Ala Asp Glu Leu Leu<br>165 170 175 | | 528 |
| agg ttg ttc ttg agg gcg ctg ggg ctc acc ggc gag gag gtc gcc gga<br>Arg Leu Phe Leu Arg Ala Leu Gly Leu Thr Gly Glu Glu Val Ala Gly<br>180 185 190 | | 576 |
| gtc gag gcg gag agg agg atc ggc gag agg atg acg gcg acg gtg cac<br>Val Glu Ala Glu Arg Arg Ile Gly Glu Arg Met Thr Ala Thr Val His<br>195 200 205 | | 624 |
| ctc aac tgg tac ccg agg tgc ccg gag ccg cgg cga gcg ctg ggg ctc<br>Leu Asn Trp Tyr Pro Arg Cys Pro Glu Pro Arg Arg Ala Leu Gly Leu<br>210 215 220 | | 672 |
| atc gcg cac acg gac tcg ggc ttc ttc acc ttc gtg ctc cag agc ctc<br>Ile Ala His Thr Asp Ser Gly Phe Phe Thr Phe Val Leu Gln Ser Leu<br>225 230 235 240 | | 720 |
| gtc ccg ggg ctg cag ctg ttc cgt cga ggg ccc gac cgg tgg gtg gcg<br>Val Pro Gly Leu Gln Leu Phe Arg Arg Gly Pro Asp Arg Trp Val Ala<br>245 250 255 | | 768 |
| gtg ccg gcg gtg gcg ggg gcc ttc gtc gtc aac gtc ggc gac ctc ttc<br>Val Pro Ala Val Ala Gly Ala Phe Val Val Asn Val Gly Asp Leu Phe<br>260 265 270 | | 816 |
| cac atc ctc acc aac ggc cgc ttc cac agc gtc tac cac cgc gcc gtc<br>His Ile Leu Thr Asn Gly Arg Phe His Ser Val Tyr His Arg Ala Val<br>275 280 285 | | 864 |
| gtg aac cgc gac cgc gac cgg gtc tcg ctc ggc tac ttc ctc ggc ccg<br>Val Asn Arg Asp Arg Asp Arg Val Ser Leu Gly Tyr Phe Leu Gly Pro<br>290 295 300 | | 912 |
| ccg ccg gac gcc gag gtg gcg ccg ctg ccg gag gcc gtg ccg gcc ggc<br>Pro Pro Asp Ala Glu Val Ala Pro Leu Pro Glu Ala Val Pro Ala Gly<br>305 310 315 320 | | 960 |
| cgg agc ccc gcc tac cgc gct gtc acg tgg ccg gag tac atg gcc gtc<br>Arg Ser Pro Ala Tyr Arg Ala Val Thr Trp Pro Glu Tyr Met Ala Val<br>325 330 335 | | 1008 |
| cgc aag aag gcc ttc gcc acc ggc ggc tcc gcc ctc aag atg gtc tcc<br>Arg Lys Lys Ala Phe Ala Thr Gly Gly Ser Ala Leu Lys Met Val Ser<br>340 345 350 | | 1056 |
| acc gac gcc gcc gcc gcc gac gaa cac gac gac gtc gcc gcc gcc<br>Thr Asp Ala Ala Ala Ala Asp Glu His Asp Asp Val Ala Ala Ala<br>355 360 365 | | 1104 |
| gcc gac gtc cac gca taa<br>Ala Asp Val His Ala<br>370 | | 1122 |

<210> SEQ ID NO 5
<211> LENGTH: 1948
<212> TYPE: DNA
<213> ORGANISM: Oryza sativa
<220> FEATURE:
<223> OTHER INFORMATION: genomic DNA sequence
<220> FEATURE:
<221> NAME/KEY: intron
<222> LOCATION: (811)..(909)
<220> FEATURE:
<221> NAME/KEY: intron
<222> LOCATION: (1072)..(1461)

<400> SEQUENCE: 5

| | |
|---|---|
| ctcgaggatc gaaaccaaaa ttaagggagc acaaaaaact atgacaaatg tttagttctg | 60 |
| acaatgaact aaattagaac aaagcttgat ccgatcctat ccatttctga ttttgtgccg | 120 |
| aacgatgcgg agagaagtta gttttttgta gataatgcaa gcccaaattt agccatgcta | 180 |
| tctcgttatt aatcacgcga aagaaatggt catgccaaca aattaattta tcgtacatca | 240 |

-continued

```
ctagtcacag gcttttgtgc gttagccaac gagttcatgc agatcatgac atcgtcgtcg      300
acctcgccga cctcgaccgc tggccgccgc cgcacacaat ggcgtcaccg ccgcctactt      360
caacttccgc ggggcggagc gcgtgccgga gtcgcacgtg tggaagggga tgcacgagaa      420
ggacaccgcg ccggtggcgg cggcggacgc ggacggcggc gacgcggtgc cggtggtgga      480
catgagcggc ggcgacgacg ccgcggtggc ggcggtggcg cgcgcggcgg aggagtgggg      540
cgggttcctg ctcgtcgggc acggcgtgac cgcggaggcc ctggcgcgcg tcgaggcgca      600
ggcggcgcgg ctgttcgcgc tgccggcgga cgacaaggcg cgcggggcgc ggcggcccgg      660
cggcgggaac accggctacg gcgtgccgcc gtacctcctc cggtacccga agcagatgtg      720
ggccgagggc tacaccttcc ctcccctgc catccgcgac gagttccgcc gcgtctggcc       780
cgacgccggc gacgactacc accgcttctg gtacgcgttt accgccgatc gatcgatcga      840
tccgccattg cttgcatgca actaacctag ctagcttccg cgcgtgttcg tccgatccgg      900 cccgccagc tccgccatgg aggagtacga ctcgtcgatg agagctctgg gcgagaggct       960
cctcgccatg ttcttcaagg cgctcgggct cgccggcaac gatgcccccg gcggcgagac     1020
cgagcggaag atccgcgaaa cgttgacgtc gtcgacgatt cacctcaaca tgtatgtaaa     1080
ctcatatgga tgtggatttt ctatgcatag atgccatagc actgcaccca tcatttacat     1140
acgattttga gaaatataaa gtttataaac aagctatatt taatctacaa ctaaaaaaac     1200
aaaaataata aaatcaggca ataaatacta gtaaaatttg ttatttttac ttcgtgtgta     1260
ggtcgaattt aattttacat atttatatag tgtttttatac tattattgta atctatctta    1320
tcaaattcta tgattttta taactattta aactacatgt atgatacaca attagaaaat     1380
acttttccat acaaatatat cttcacatgc aatggtgttt ggagctgatc gacacgtgtc    1440
actctgacat ggccacacgc aggttcccta ggtgtccaga tccagaccgg gtggtcgggc    1500
tggcggcgca cacggactca ggcttcttca ccttcatcct gcagagcccc gtgccggggt    1560
tgcagctgct ccgccaccgg ccggaccggt gggtgacggt tccggggacg ccgggggcgc    1620
tcatcgtcgt cgtcggcgat ctcttccatg tgctcaccaa cgggcgcttc cacagcgtgt    1680
tccaccgcgc cgtcgtgaac cgggagagag accggatctc catgccctac ttcctcggtc    1740
cgccggccga catgaaggtg acacctctcg tggcggcggg gtcgccggag agcaaggccg    1800
tgtatcaggc cgtgacatgg ccggagtaca tggctgtaag ggataagttg ttcgggacaa    1860
atatatcggc gttgagcatg attcgagtag cgaaggaaga ggacaaggag agttagaact    1920
atggtatgat tgcaattatc catgccag                                         1948
```

<210> SEQ ID NO 6
<211> LENGTH: 2112
<212> TYPE: DNA
<213> ORGANISM: Oryza sativa
<220> FEATURE:
<223> OTHER INFORMATION: genomic DNA sequence
<220> FEATURE:
<221> NAME/KEY: intron
<222> LOCATION: (789)..(899)

<400> SEQUENCE: 6

```
ttttttcctc tccaaatcta ttaattaatg atccatttca attcttcatc actgatttat       60
tcaccaatta attctctctt tttttttct tccactacgc tccaaaactt ctctccctat       120
atatacctct cccttgtact tgtccagttc ttacactcgt ctcactttac tactcattcc      180
actattgtaa agtcatagaa aaaatttata tagagagaaa aaattagtgt ttgttattgt      240
```

```
tactggcttt ctgccagacg agacgagcga gcgcgcgagt gtgttcctct ctgagtcatc    300
tcgtcgtcgt cggcgatgcc gacgccgtcg cgcttgaaga acccgctctg cttcgacttc    360
cgggcggcga ggcgggtgcc ggagacgcac gcgtggccgg ggctggacga ccacccggtg    420
gtggacggcg gcgcggcgg cggcgaggac gcggtgccgg tggtggacgt cagggcgggc    480
gacgcggcgg cgcgggtggc gcgggcggcg gagcagtggg gcgcgttcct tctggtcggg    540
cacggcgtgc cggcggcgct gctgtcgcgc gtcgaggagc gcgtcgcccg cgtgttctcc    600
ctgccggcgt cggagaagat gcgcgccgtc cgcggccccg gcgagccctg cggctacggc    660
tcgccgccca tctcctcctt cttctccaag ctcatgtggt ccgagggcta caccttctcc    720
ccttcctccc tccgctccga gctccgccgc ctctggccca gtccggcga cgactacctc    780 ctcttctggt atatatacat atatatatac tctcccatgc attccatgca catacactct    840
acgtatatat ctacctctac gtatatatct acgtattgat ctacgtataa tatacgcagt    900
gacgtgatgg aggagtttca caaggagatg cggcggctag ccgacgagtt gctgaggttg    960
ttcttgaggg cgctgggggct caccggcgag gaggtcgccg gagtcgaggc ggagaggagg   1020
atcggcgaga ggatgacggc gacggtgcac ctcaactggt acccgaggtg cccggagccg   1080
cggcgagcgc tggggctcat cgcgcacacg gactcgggct tcttcacctt cgtgctccag   1140
agcctcgtcc cggggctgca gctgttccgt cgagggcccg accggtgggt ggcggtgccg   1200
gcggtggcgg gggccttcgt cgtcaacgtc ggcgacctct tccacatcct caccaacggc   1260
cgcttccaca gcgtctacca ccgcgccgtc gtgaaccgcg accgcgaccg ggtctcgctc   1320
ggctacttcc tcggcccgcc gccggacgcc gaggtggcgc cgctgccgga ggccgtgccg   1380
gccggccgga gccccgccta ccgcgctgtc acgtggccgg agtacatggc cgtccgcaag   1440
aaggccttcg ccaccggcgg ctccgccctc aagatggtct ccaccgacgc cgccgccgcc   1500
gccgacgaac acgacgacgt cgccgccgcc gccgacgtcc acgcataagc tatagctact   1560
agctacctcg atctcacgca aaaaaaaaa gaaacaatta atagagcaaa aaaaaaaga    1620 aacaattaat agagcaaaaa aaaaagaag agaaaatggt ggtacttgtg tttaaggttt    1680
cctccatgca aaatggtttg catgcatgca tgcaaagcta gcatctgcag ctgcaagaat   1740
tacaagagca gagaagcaga cagctagatg gagataatta attaattaat taatctaatt    1800
aagcatgcaa taattaagat tattattctg atttcagaac tgaaaaaaaa agtgtggtta    1860
attaattatt ggttaggctt aatttttatct agatgtagaa aaagaatcaa gatcttcaag   1920
caagagagaa gaggatcgaa gaagaaggaa agaaaacga aaggacatg ctgtgttgtc     1980 tcttctagtt gtaccctggc tgctgattaa gtgctttgtt ttgttgctgc aagcttgtcg   2040
ttactgatta ttagttagtt atgcatctaa ttgattaaac taatctgttt ggcattttgg   2100
ctcgaggtcg ac                                                        2112
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: 3, 6, 12, 15
<223> OTHER INFORMATION: n = A,T,C or G

```
<400> SEQUENCE: 7
gtngtnaarg tnggngarrt                                                      20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:an
      artificially synthesized primer sequence
<220> FEATURE:
<221> NAME/KEY: misc_feature
<222> LOCATION: 15, 18
<223> OTHER INFORMATION: n = A,T,C or G

<400> SEQUENCE: 8
ayytartcrt tggangtnac                                                      20
```

GIBBERELLIN 3β-HYDROXYLASE GENES OF RICE AND USES THEREOF

This application claims the benefit of prior-filed Japanese Patent Application 11/361608 (filed Dec. 20, 1999) entitled "Rice-origin Gibberellin 3β-Hydroxylase Genes and Utilization Thereof". The entire content of the above-referenced application is incorporated herein by reference.

TECHNICAL FIELD

The present invention relates to rice genes involved in gibberellin biosynthesis and uses of these genes.

BACKGROUND ART

Multicellular organisms have a large number of specialized organs and tissues that are assembled to form a functional unit. Coordination of various parts of an organism is achieved by chemical messenger substances termed hormone. Plant hormones are naturally occurring substances, effective in very small amounts that act as signals to stimulate or inhibit growth or regulate development. Nowadays, the following molecules are generally recognized to be plant hormones: auxins, gibberellins, cytokinins, abscisic acid, brassinolide, and ethylene.

In animals, hormones are usually synthesized in special glands and distributed via the bloodstream within the organism. Thus, they reach the target site and responsive tissues that are ready to react. There they trigger specific regulatory processes. This classical concept of hormones that was originally developed for animals was extended to higher plants. In many cases, plant hormones are active in specific target tissues, which are often different from the tissues in which the hormone is produced. However, all the plant hormones can also be detected in many tissues of the multicellular plant. This indicates that there is frequently no obligatory division between the site of synthesis and the site of action of plant hormones. If required, they are able to act on the same cells (tissues) in which they were synthesized. Thus, understanding the control of plant hormone synthesis is important in determining the relationship between synthesis and action.

Gibberellins (GAs) were originally discovered as phytotoxins in 1920s by Japanese phytopathologists. The pathogenic fungus, *Gibberella fujikuroi*, infects rice plants and secretes a compound that causes pathological longitudinal growth (Bakanae "mad seedling disease"). Between 1935 and 1938 the active substance was isolated and crystallized. It was called "gibberellin." Later researches showed that GAs are also synthesized by higher plants and are very important in the regulation of growth and in differentiation processes.

The basic structure of approximately 80 GAs identified up to 1992 is the tetracyclic ring system of the ent-gibberellan (FIG. 1a). GAs contain diterpenoid carboxylic acids produced mainly from mevalonic acid via cyclization of geranylgeranyl pyrophosphate (FIG. 1b). Most of the GAs are inactive in promoting plant development. In many plants, biologically active GAs, which act as plant growth regulators, are $GA_1$ and $GA_4$. They can control various developmental processes, including seed germination, stem elongation, flowering, and fruit development. Thus, various modified plants that are industrially useful can be generated by modifying GA biosynthesis.

The role of GAs as mediators of environmental stimuli has been well established. Physical factors, such as light and temperature, can modify GA metabolism by changing the flux through specific step in the pathway. For example, light quality (red or far-red) and intensity (high or low) affects GA biosynthesis. In lettuce seeds and cowpea epicotyls, 3-beta hydroxylation of $GA_{20}$ is enhanced by treatment with far-red light (Toyumasu et al., (1992) Plant Cell Physiol. 33, 695–701). In addition, when pea seedlings are grown in low irradiance (40 μmol/m²s), $GA_{20}$ content increases sevenfold compared with plants grown in high irradiance (386 μmol/m²s), whereas in plants grown in the dark, the $GA_{20}$ content is reduced as compared to that in high irradiance (Gawronska et al., (1995) Plant Cell Physiol. 36, 1361–1367).

In spite of many attempts to implicate GA metabolism in phytochrome-mediated or light intensity-mediated changes in growth rate, supporting evidence is sparse. The mechanism(s) underlying these regulatory processes will eventually be understood as a result of the current advances in the molecular biology of GA biosynthesis.

Despite considerable efforts, the site of synthesis of bioactive GAs and their mode of action in specific cells and tissues has not been clarified. Based on experiments in which plants were supplemented with $^{14}$C-labelled GAs, it is thought that they are translocated in a non-polar manner throughout the plant. More recently, grafting experiments with dwarf and wild-type pea plants indicated that $GA_1$, one of the bioactive GA, is not transported, unlike its precursor, $GA_{20}$, (Proebsting et al. (1992) Plant Physiol. 100, 1354–1360; Reid et al., (1983) J. Exp. Bot. 34, 349–364). Quantitative analyses using GC-MS and bioassays with dwarf pea plants have revealed that GAs are mainly present in actively growing and elongating tissues such as shoot apices, young leaves, and flowers (Jones and Phillips, (1966) Plant Physiol. 41, 1381–1386; Potts et al. (1982) Physiol. Plant, 55, 323–328: Kobayashi et al., (1988) Agric. Biol. Chem. 52, 1189–1194). However the exact amount of each GA in a specific tissue is difficult to determine because most GAs are present in very small amounts and most are not bioactive. Therefore, a new approach is needed to clarify the location of synthesis of bioactive GAs.

According to progress in molecular biology and genetic engineering, almost of the genes encoding GA biosynthetic enzymes so far have been cloned from various plant species. The studies of these clones have shown that GA responsive dwarf mutants lack the respective GA biosynthetic enzymes (FIG. 1b). Their expression profile indicates that the pathway is strictly regulated during development. Among these genes, GA1 from Arabidopsis, which encodes copalyl diphosphate synthase (CPS), an enzyme active early in GA biosynthesis, is highly expressed in rapidly growing tissues, e.g., the shoot apex, root tips, and flowers (Silverstone et al., (1997) Plant J. 12, 9–19). GA C-20 oxidase, which catalyzes a late step in the GA biosynthetic pathway and constitutes a small gene family, is specifically expressed in stems and developing seeds of Arabidopsis, pea, and bean where GA is required for development. They are negatively regulated by treatment with $GA_3$ (Phillips et al., (1995) Plant Physiol. 108, 1049–1057; Garcia-Martinez et al., (1997) Plant Mol. Biol. 33, 1073–1084).

These observations lead the present inventors to speculate that GA action in various organs may depend upon the amount of endogenous GA present, which in turn depends on the regulation of expression of GA biosynthetic enzymes, rather than on the translocation of bioactive GA to the site of GA action. However, analysis of the expression of CPS or GA C-20 oxidase provides no direct evidence of the site of synthesis of bioactive GAs and regulation of bioactive GA levels because bioactive GAs are synthesized by 3β-hydroxylation which is catalyzed by GA 3β-hydroxylase.

As described above, 3β-hydroxylase catalyzes the conversion of the $GA_{20}$ and $GA_9$ to $GA_1$ and $GA_4$, respectively, at the final step in the synthesis of bioactive GAs (FIG. 1b). The enzymology of 3β-hydroxylase has not yet been completely clarified. However, the 2-oxoglutarate-binding region is essential for its activity, indicating that GA 3β-hydroxylase has the typical properties of a 2-oxoglutarate-dependent dioxygenase. Certain GA 3β-hydroxylase may be multifunctional; the enzyme from pumpkin endosperm catalyzes both 2β and 3β hydroxylation (Lange et al., (1997) Plant Cell, 9, 1459–1467). Maize dwarf-1,3β-hydroxylase has also been considered to be multifunctional and it catalyzes three hydroxylation steps in the maize GA biosynthetic pathway (Spray et al., (1996) Proc. Natl. Acad. Sci. 93, 10515–10518). But the nature of these GA 3β-hydroxylases is still not well known.

DISCLOSURE OF THE INVENTION

The present invention provides novel GA 3β-hydroxylase genes from rice and uses of the genes, especially for production of plants whose plant type has been modified.

For the isolation of GA 3β-hydroxylase genes from rice, the present inventors first performed PCR using degenerate primers designed based on the conserved region of dicot GA 3β-hydroxylases with the rice genomic DNA as a template. Then, using a fragment of the genomic DNA encoding GA 3β-hydroxylase thus obtained as a probe, the present inventors screened the rice genomic library to obtain several clones. These clones were divided into two groups based on their restriction maps, and one clone of each group was entirely sequenced. As a result, the present inventors found out that each of these clones encodes one rice GA 3β-hydroxylase.

Then, to obtain cDNA fragments based on the nucleotide sequence of each clone, the present inventors performed RT-PCR using the total RNA isolated from the rice seedlings (rice shoot apices) or unopened flowers, thereby obtaining the full-length cDNA clones encoding GA 3β-hydroxylases (designated "Os3β-1" and "Os3β-2", respectively). Furthermore, using primers designed based on the genomic DNA sequences thus obtained, the present inventors performed RT-PCR with the total RNA isolated from the rice seedlings (shoot apices) or unopened flowers as a template and succeeded in obtaining the cDNA clones encoding the complete rice GA 3β-hydroxylase.

Since in rice the d18 mutant is known as a GA-responsive dwarf cultivar, the present inventors examined whether the rice GA 3β-hydroxylase clone thus isolated corresponds to the D18 gene. RFLP (Restriction Fragment Length Polymorphism) analysis and direct analysis of the nucleotide sequence of d18 allele proved that, of the two isolated rice genes, the Os3β-2 gene is the causative gene of the d18 mutation. In addition, the difference between the Os3β-1 gene and the Os3β-2 gene in their expression plant parts indicated that the Os3β-1 protein is involved in a different biosynthetic pathway of bioactive GAs than the Os3β-2 protein.

Furthermore, the present inventors succeeded in producing a dwarfed rice plant compared with a wild type plant by suppressing the expression of the Os3β-2 gene in rice plant utilizing the antisense DNA of the gene.

As described above, the present inventors succeeded in isolating a novel GA 3β-hydroxylase gene from rice, and found that a plant with modified plant type compared with a wild type plant can be produced by suppressing the expression of the gene.

In more detail, the present invention is to provide:

(1) a DNA encoding a protein having the gibberellin 3β-hydroxylase activity according to any one of the following (a) through (c):
  (a) a DNA encoding a protein comprising the amino acid sequence set forth in SEQ ID NO: 1 or 2,
  (b) a DNA comprising the coding region of the nucleotide sequence set forth in SEQ ID NO: 3 or 4.
  (c) a DNA encoding a protein comprising the amino acid sequence set forth in SEQ ID NO: 1 or 2 in which one or more amino acids are substituted, deleted, added, and/or inserted;

(2) a DNA encoding an antisense RNA complementary to the DNA according to (1) or its transcription product;

(3) a DNA encoding an RNA having the ribozyme activity to specifically cleave the transcription product of the DNA according to (1);

(4) a DNA encoding an RNA that suppresses the expression of endogenous DNA according to (1) by co-suppression when the endogenous DNA is expressed in plant cells;

(5) a vector containing the DNA according to any one of (1) through (4);

(6) a transformed plant cell harboring the DNA according to any one of (1) through (4) in an expressible state;

(7) a transgenic plant containing the transformed plant cell according to (6);

(8) a propagative material of the transgenic plant according to (7);

(9) a protein encoded by the DNA according to (1);

(10) a method for producing the protein according to (9), wherein said method comprises culturing the transformed cells carrying the DNA according to (1) in an expressible state, and recovering the expressed protein from said cells or the culture supernatant thereof;

(11) a method for modifying the plant growth, wherein said method comprises controlling the expression level of the DNA according to (1) in plant cells; and

(12) a method for modifying a plant type, wherein said method comprises controlling the expression level of the DNA according to (1) in plant cells.

The present invention provides novel GA 3β-hydroxylases isolated from rice plant and DNAs encoding these enzymes. Nucleotide sequences of cDNAs GA 3β-hydroxylase genes from rice, Os3β-1 and Os3β-2, isolated by the present inventors and included in the DNA of this invention, are set forth in SEQ ID NOs: 3 and 4, respectively. The nucleotide sequence of the genomic DNAs of these cDNAs are shown in SEQ ID NOs: 5 and 6, respectively. In addition, amino acid sequences of the "Os3β-1" and "Os3β-2" proteins are set forth in SEQ ID NOs: 1 and 2, respectively.

Consistent with the previous classification of the 3β-hydroxylase as 2-oxoglutarate-dependent dioxygenases (2-ODDs), both "Os3β-1" and "Os3β-2" proteins originating in rice contained all of the domains characteristic of plant 2-ODDs (Prescott, A. G. (1993) J. Exp. Bot. 44, 849–861; de Carolis and Luca (1994) Phytochemistry 36, 1093–1107). Amongst all of the published sequences, coding regions of both clones show the highest homology with GA 3β-hydroxylases. Especially, these regions are highly conserved (position of 240 to 247 and 302 to 307 in Os3β-1, 222 to 229 and 285 to 290 in Os3β-2) and may act as the binding site of iron and the cofactor, 2-oxoglutarate. These proteins also have the conserved motif (Met-Trp-X-Glu-Gly-X-Thr), which is unique to the GA 3β-hydroxylase (position of 144 to 150 in Os3β-1, 127 to 133 in Os3β-2). Sequence comparison with dicot GA 3β-hydroxylases and other dioxygenases suggests that both cDNA clones isolated by the present inventors encode rice GA 3β-hydroxylases.

Mapping of Os3β-2 and genomic Southern analysis indicated that Os3β-2 corresponds to the D18 gene. The rice d18 mutants are GA-responsive dwarf cultivars, including Hosetu-waisei, Akibare-waisei, Kotake-tamanishiki, and Waito-C (FIG. 2). Many dwarf alleles so far have been identified. The Os3β-2 protein is assumed to be also involved in the internodal growth of plants via synthesis of bioactive GAs.

Analyses on the levels of endogenous GAs in different organs at various growth stages have revealed that 13-hydroxylated gibberellins ($GA_{19}$, $GA_{20}$, $GA_1$) are dominant in vegetative organs, while non-13-hydroxylated gibberellins ($GA_{24}$, $GA_9$, $GA_4$) are specifically accumulated in reproductive growth organs, especially in anthers. This indicates that the biosynthetic pathway for bioactive GAs is organ-specific (Kurogouchi, S. et al. (1979) Planta 146, 185–191; Kobayashi, M. et al. (1984) Agric. Biol. Chem. 48, 2725–2729; Kobayashi, M. et al, (1988) Agric. Biol. Chem. 52, 1189–1194). Expression patterns of Os3β-2 (D18) and Os3β-1 are consistent with this speculation. Indeed, the Os3β-2 mRNA was in high level in stems, young leaves, and inflorescence meristems, while the Os3β-1 mRNA was specifically observed in flowers. These consistencies indicate that products of Os3β-2 and Os3β-1 may have the substrate-specificity for $GA_{20}$ and $GA_9$, respectively.

Expressions of Os3β-2 and Os3β-1 are also consistent with the distribution of bioactive GAs in rice. Breeding and quantitative analyses revealed that $GA_1$ was high in young leaf tissues which are the most active sites of gibberellin biosynthesis (Choi, Y.-H. et al. (1995) Plant Cell Physiol. 36(6), 997–1001), and the highest expression of Os3β-2 was also observed in young leaves. Interestingly, the expression of Os3β-2 in shoot apices was at moderate levels as compared with other organs of rice, nevertheless many genes for GA biosynthesis, such as GA1 from *Arabidopsis* and Nty from tobacco, are strongly expressed in the actively dividing and elongating tissues, like shoot apices and roots (Silverstone et al. (1997) Plant J. 12, 9–19). This discrepancy suggests that the organ activity to synthesize GAs may differ between monocotyledonous and dicotyledonous plants. On the other hand, the endogenous level of $GA_4$ is extremely high in anthers at the flowering stage (Kobayashi, M. et al. (1988) Agric. Biol. Chem. 52, 1189–1194; Kobayashi, M. et al. (1990) Plant Cell Physiol. 31(2), 289–293). This fact is consistent with the specific expression of Os3β-1 in flowers. This consistency may indicate that $GA_4$ is synthesized in anthers by the action of the Os3β-1 protein. Therefore, the Os3β-2 and Os3β-1 proteins may be involved in different biosynthetic pathways of bioactive GAs.

In fact, the Os3β-1 protein catalyzed the production of $GA_4$ (3β-hydroxylation), $GA_7$ (2,3-unsaturation and 3β-hydroxylation), and $GA_{34}$ (2β-hydroxylation) with $GA_9$ as its substrate (FIG. 9), and similar results were obtained with $GA_{20}$ as the substrate. In addition, with $GA_5$ and $GA_{44}$ as its substrate, the protein produced the corresponding 3β-hydroxylated gibberellins, $GA_3$ and $GA_{88}$, respectively. Furthermore, the Os3β-2 protein catalyzed, with $GA_5$, $GA_9$, $GA_{20}$, and $GA_{44}$ as the substrates, the production of the corresponding 3β-hydroxylated gibberellins, $GA_3$, $GA_4$, $GA_1$, and $GA_{38}$, respectively (FIG. 10) (Example 5).

Several reports mention the necessity of bioactive GAs not only for the stem elongation but also for a variety of other plant growth processes. For example, as to the floral organs, the male-sterile phenotype shown in an *Arabidopsis* GA-deficient mutant, gal-3 (Koornneef, M. and Van der Veen, J. H. (1980) Theor. Appl. Genet. 58, 257–263), and the arrest of anther growth at an early stage without formation of viable pollen grains in tomato mutants, stamenless-2 and gib-1 (Sawhney (1974) J. Exp. Bot. 25, 1004–1009; Jacobsen and Olszewski (1996) Proc. Natl. Acad. Sci. U.S.A. 93, 9292–9296), have been reported.

Since the proteins of the present invention are thought to be involved in the biosynthesis of bioactive GAs, they can be used in manufacturing bioactive GAs. Furthermore, as described below, the plant growth can be modified by regulating expression levels of these proteins in plants. For example, a plant having a different plant type from a wild type can be produced.

The protein of this invention can be prepared as a recombinant protein via methods known to those skilled in the art utilizing the gene recombination techniques or as a natural protein. A recombinant protein can be prepared, as described below, for example, by inserting DNA (e.g., SEQ ID NOs: 3 and 4) encoding the protein of this invention into an appropriate expression vector and purifying the protein from cells transformed with the vector. A natural protein can be prepared, for example, by immunizing suitable animals with the prepared recombinant protein or its partial peptide, binding the thus prepared antibody to a column for affinity chromatography, contacting the column with extracts prepared from tissues of tobacco and rice expressing the protein of this invention, and purifying the protein binding to the column.

The protein of this invention includes wild type proteins (SEQ ID NOs: 1 and 2) in which partial amino acid residues are modified, while retaining the function of the wild type proteins. An example of the method for preparing such modified proteins well known to those skilled in the art include the site-directed mutagenesis method (Kramer, W. & Fritz, H.-J. Oligonucleotide-directed construction of mutagenesis via gapped duplex DNA. Methods in Enzymology, 154: 350–367, 1987). Amino acid mutations may also occur spontaneously. The protein of this invention thus include proteins that retain the GA 3β-hydroxylase activity of the wild-type protein and those that are modified via substitution, deletion, addition, and/or insertion of one or more amino acid residues in the amino acid sequence of the wild type protein. There is no particular limitation on the site and number of such amino acid modifications in the protein so far as the modified protein retains the GA 3β-hydroxylase activity. The number of amino acid that can be modified is usually not more than 50 amino acid residues, preferably not more than 30, more preferably not more than 10, and most preferably not more than 3 amino acid residues.

Herein, the term "GA 3β-hydroxylase activity" refers to the activity to synthesize $GA_1$ or $GA_4$ as the reaction product when $GA_{20}$ or $GA_9$ is used as a reaction substrate and ferrous iron and 2-oxoglutarate are used as cofactors. The activity can be detected, for example, as follows. In general, cDNA obtained is inserted into an expression vector and overexpressed as a fusion protein in *E. coli*. Using the cell extract thus obtained (as an enzyme solution), the reaction is performed in vitro with $GA_{20}$ or $G_9$ as a reaction substrate in the presence of the co-factors, ferrous ion and 2-oxoglutarate, and finally the reaction product ($GA_1$ or $GA_4$) is confirmed by GC-MS.

The present inventors isolated cDNA and genomic DNA encoding the above proteins. Therefore, DNAs encoding the protein of this invention include both cDNA and genomic DNA so far as they encode these proteins. When DNAs encoding the Os3β-2 and Os3β-1 proteins are cDNAs, the DNAs can be prepared by RT-PCR using respective primers designed based on the information of nucleotide sequences set forth in SEQ ID NOs: 3 and 4 and the total RNA isolated from seedlings (shoot apices of rice) or unopened flowers as a template. Furthermore, the genomic DNA can be prepared by PCR using respective primers designed based on the information of nucleotide sequences set forth in SEQ ID NOs: 5 and 6 and the rice genomic DNA as a template.

DNAs encoding the protein of the present invention can be used, for example, for producing recombinant proteins. Production of recombinant proteins can be carried out described below. First, a full-length cDNA is synthesized by RT-PCR using primers provided with restriction enzyme sites and subcloned into multi-cloning sites of the pMAL-c2 expression vector (NEB). This construct is used to transform Escherichia coli strain BL21 cells (protease-deficient strain) by standard methods. Using the transformant thus obtained, the protein is induced. E. coli are cultured (by shaking) in a 2×YT medium containing 0.2% glucose at 37° C. When an $OD_{600}$ value reaches around 0.6, IPTG is added to a final concentration of 1 mM, and culturing is further continued at 18° C. for 24 h. Extraction of an enzyme solution is performed as follows. After culturing, cells are collected and lysed in a suspension buffer (50 mM Tris-HCl (pH 8.0) containing 10% glycerol, 2 mM DTT, and 1 mg/ml lysozyme). The cell suspension is allowed to stand at 4° C. for 30 min, and then incubated at −80° C. until it becomes completely frozen. The frozen suspension is thawed and sonicated for 30 s twice at 5-min intervals at the MAX level with the Sonicator (Heat Systems—Ultrasonics, Inc., Model W-225R). The suspension thus treated is centrifuged (at 15,000 rpm and 4° C. for 20 min), and the supernatant is used as a crude enzyme solution.

Furthermore, preparation of the purified protein can be carried out, by expressing the protein of this invention in E. coli (or the like) as a fusion protein with the histidine tag, maltose-binding protein, or glutathione-S-transferase (GST), and subsequently purifying them on a nickel column, an amylose-column, or a GST-glutathione column, respectively. Then, after the purification, the above-described tags can be cleaved off using limited proteases, such as, thrombin and factor Xa as required.

As described above, the genes isolated by the present inventors are assumed to be involved in the plant growth through the production of bioactive GAs. Therefore, plant growth may be controlled by regulating the expression of these genes. Since Os3β-2 in particular is thought to be involved in the internodal growth of plants, this gene may be utilized in the control of plant stature. Control of plant stature provides a variety of industrial advantages.

For example, the shortened stature caused by suppressing the expression of the gene of this invention in a plant can make the plant resistant to bending thereby increasing the fruit weight. Furthermore, the shortened stature makes the size of the plant per stub more compact so that the number of plants to be planted per unit area can be increased. This dense planting is highly important in the production of agricultural products including rice, wheat, maize, etc., in particular. DNA encoding the protein of the present invention may be applicable to dwarf flowering plants, dwarf fruit trees, etc. Male sterile traits may be induced by suppressing the expression of the Os3β-1 gene in flowers.

On the other hand, the yield of plants as a whole may be enhanced by lengthening plant stature through the elevated expression of genes of this invention within the plants. This is useful for improving feed crop yields as a whole in particular.

In the present invention, a variety of methods known to those skilled in the art are available for suppressing the expression of genes of this invention to control plant growth. Herein, "suppression of expression of genes" includes suppressions of both gene transcription and translation into proteins, and includes not only complete suppression but also decrease in the gene expression.

The expression of a specific endogenous gene in plants can be suppressed by conventional methods utilizing antisense technology. Ecker et al. were the first to demonstrate the effect of an antisense RNA introduced by electroporation in plant cells by using the transient gene expression method (Ecker, J. R. and Davis, R. W. (1986). Proc. Natl. Acad. Sci. USA 83, 5372). Thereafter, the target gene expression was reportedly reduced in tobacco and petunias by expressing antisense RNAs (van der Krol, A. R. et al. (1988). Nature 333, 866). The antisense technique has now been established as a means to suppress target gene expression in plants.

Multiple factors cause antisense nucleic acid to suppress the target gene expression. These include inhibition of transcription initiation by triple strand formation; suppression of transcription by hybrid formation at the site where the RNA polymerase has formed a local open loop structure; transcription inhibition by hybridization with the RNA being synthesized; suppression of splicing by hybrid formation at the junction between an intron and an exon; suppression of splicing by hybrid formation at the site of spliceosome formation; suppression of mRNA translocation from the nucleus to the cytoplasm by hybridization with mRNA; suppression of splicing by hybrid formation at the capping site or at the poly A addition site; suppression of translation initiation by hybrid formation at the binding site for the translation initiation factors; suppression of translation by hybrid formation at the site for ribosome binding near the initiation codon; inhibition of peptide chain elongation by hybrid formation in the translated region or at the polysome binding sites of mRNA; and suppression of gene expression by hybrid formation at the sites of interaction between nucleic acids and proteins. These factors suppress the target gene expression by inhibiting the process of transcription, splicing, or translation (Hirashima and Inoue, "Shin Seikagaku Jikken Koza (New Biochemistry Experimentation Lectures) 2, Kakusan (Nucleic Acids) IV, Idenshi No Fukusei To Hatsugen (Replication and Expression of Genes)," Nihon Seikagakukai Hen (The Japanese Biochemical Society Ed.), Tokyo Kagaku Dozin, pp. 319–347, (1993)).

An antisense sequence used in the present invention can suppress the target gene expression by any of the above-mentioned mechanisms. If an antisense sequence is designed to be complementary to the untranslated region near the 5' end of the gene's mRNA; it will effectively inhibit translation of a gene. Additionally, it is also possible to use sequences that are complementary to the coding regions or to the untranslated regions on the 3' side. Thus, the antisense DNA used in the present invention includes a DNA having antisense sequences against both the untranslated regions and the translated regions of the gene. The antisense DNA to be used is connected downstream from an appropriate promoter, and, preferably, a sequence containing the transcription termination signal is connected on the 3' side. The DNA thus prepared can be transfected into the desired plant by known methods. The sequence of the antisense DNA is preferably a sequence complementary to the endogenous gene (or the homologue) of the plant to be transformed or a part thereof, but it need not be perfectly complementary so long as it can effectively inhibit the gene expression. The transcribed RNA is preferably not less than 90%, and most preferably not less than 95% complementary to the transcribed products of the target gene. In order to effectively inhibit the expression of the target gene by means of an antisense sequence, the antisense DNA should be at least 15 nucleotides long or more, preferably 100 nucleotides long or more, and most preferably 500 nucleotides long or more. The antisense DNA to be used is generally shorter than 5 kb, and preferably shorter than 2.5 kb.

DNA encoding ribozymes can also be used to suppress the expression of endogenous genes. A ribozyme is defined as an RNA molecule that has catalytic activities. Numerous ribozymes are known in the literature, each having distinct catalytic activity. Research on the ribozymes as RNA-cleaving enzymes has enabled the designing of a ribozyme that site-specifically cleaves RNA. While some ribozymes of the group I intron type or the M1RNA contained in RNaseP consist of 400 nucleotides or more, others belonging to the hammerhead type or the hairpin type have an activity domain of about 40 nucleotides (Koizumi, Makoto and Ohtsuka, Eiko (1990). Tanpakushitsu Kakusan Kohso (Protein, Nucleic acid, and Enzyme) 35, 2191).

The self-cleavage domain of a hammerhead type ribozyme cleaves at the 3' side of C15 sequence G13U14C15. Formation of a nucleotide pair between U14 and A at the ninth position is considered important for the ribozyme activity. Furthermore, it has been shown that the cleavage also occurs when the nucleotide at the 15th position is A or U instead of C (Koizumi, M. et al. (1988). FEBS Lett. 228, 225). If the substrate-binding site of the ribozyme is designed to be complementary to the RNA sequences adjacent to the target site, one can create a restriction-enzyme-like RNA cleaving ribozyme that recognizes the sequence UC, UU, or UA within the target RNA (Koizumi, M. et al. (1988). FEBS Lett. 239, 285; Koizumi, Makoto and Ohtsuka, Eiko (1990). Tanpakushitsu Kakusan Kohso (Protein, Nucleic acid, and Enzyme), 35, 2191; Koizumi, M. et al. (1989). Nucleic Acids Res. 17, 7059). For example, in the coding region of the Nty gene, Os3β-1 gene, or Os3β-2 gene (SEQ ID NO: 3 or 4) isolated by the present inventors, there are pluralities of sites that can be used as the ribozyme target.

The hairpin type ribozyme is also useful in the present invention. A hairpin type ribozyme can be found, for example, in the minus strand of the satellite RNA of tobacco ringspot virus (Buzayan, J. M. (1986). Nature 323, 349). This ribozyme has also been shown to target-specifically cleave RNA (Kikuchi, Y. and Sasaki, N. (1992). Nucleic Acids Res. 19, 6751; Kikuchi, Yo (1992) Kagaku To Seibutsu (Chemistry and Biology) 30, 112).

The ribozyme designed to cleave the target is fused with a promoter, such as the cauliflower mosaic virus 35S promoter, and with a transcription termination sequence, so that it will be transcribed in plant cells. However, if extra sequences are added to the 5' end or the 3' end of the transcribed RNA, the ribozyme activity may be lost. In this case, one can place an additional trimming ribozyme, which functions in the cis position to perform the trimming on the 5' or the 3' side of the ribozyme portion, thereby precisely cutting the ribozyme portion from the transcribed RNA containing the ribozyme (Tairas, K. et al. (1990). Protein Eng. 3, 733; Dzaianott, A. M. and Bujarski, J. J. (1989). Proc. Natl. Acad. Sci. USA 86, 4823; Grosshands, C. A. and Cech, R. T. (1991). Nucleic Acids Res. 19, 3875; Taira, K. et al. (1991.) Nucleic Acid Res. 19, 5125). Multiple sites within the target gene can be cleaved by arranging these structural units in tandem to achieve greater effects (Yuyama, N. et al., (1992). Biochem. Biophys. Res. Commun. 186, 1271). By using such ribozymes, it is possible to specifically cleave the transcription products of the target gene in the present invention, thereby suppressing the expression of the gene.

Endogenous gene expression can also be suppressed by co-suppression through the transformation by DNA having a sequence identical or similar to the target gene sequence. "Co-suppression," as used herein, refers to the phenomenon in which, when a gene having a sequence identical or similar to the target endogenous gene sequence is introduced into plants by transformation, expression of both the introduced exogenous gene and the target endogenous gene becomes suppressed. Although the detailed mechanism of co-suppression is unknown, it is frequently observed in plants (Curr. Biol. (1997). 7, R793, Curr. Biol. (1996). 6, 810). For example, if one wishes to obtain a plant body in which the gene of the present invention is co-suppressed, the plant in question can be transformed with a DNA vector designed so as to express the gene of the present invention or DNA having a similar sequence. The gene to be used for co-suppression need not be completely identical to the target gene. However, it should have preferably 70% or more sequence identity, more preferably 80% or more sequence identity, and most preferably 90% or more (e.g. 95% or more) sequence identity.

The identity of one amino acid sequence or nucleotide sequence to another can be determined by following the BLAST algorithm by Karlin and Altschl (Proc. Natl. Acad. Sci. USA, (1993). 90, 5873–5877,). Programs such as BLASTN and BLASTX were developed based on this algorithm (Altschul et al. (1990). J. Mol. Biol.215, 403–410). To analyze a nucleotide sequences according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST programs. Specific techniques for such analysis are known in the art [available on the website of the National Center for Biotechnology Information (NCBI), National Library of Medicine, Building 38A, Bethesda Md. 20894, U.S.A.].

Modification of plant growth utilizing a DNA functioning to suppress the expression of genes of this invention may be achieved by inserting the DNA into an appropriate vector, transferring the vector into plant cells, and regenerating the transformed plant cells thus obtained. There is no particular limitation on the type of vectors so far as they are capable of expressing the inserted gene within plant cells.

For example, the promoter for the gene isolated by the present inventors may be used. A vector having a promoter (for example, 35S promoter of cauliflower mosaic virus) that enables the constitutive gene expression in plant cells may also be used. Furthermore, plant tissue-specific promoters may specifically modify particular plant tissues, for example, leaves, flowers, fruits, etc. Examples of the tissue-specific promoters are seed-specific promoters such as promoters for β-phaseolin of kidney bean (Bustos, et al. (1991). EMBO J. 10, 1469–1479) and glycinin of soy bean (Lelievre, et al. (1992). Plant Physiol. 98, 387–391); leaf-specific promoters such as promoters for the RbcS gene of pea (Lam and Chua (1990). Science 248, 471–474) and Cab 1 gene of wheat (Gotorn, et al. (1993). Plant J. 3, 509–518), root-specific promoters such as promoters for the TobRB7 gene of tobacco (Yamamoto, et al. (1991). Plant Cell 3, 371–382) and rolD gene of *Agrobacterium rhizogenes* (Elmayan and Tepfer (1995). Transgenic Res. 4, 388–396). It is also possible to use a vector having a promoter inducibly activated by exogenous stimuli.

Although there is no particular limitation on the type of plant cells into which a vector is inserted, rice and tobacco, from which the genes of the present invention are derived, are particularly preferred. Herein, the term "plant cells" includes plant cells in a variety of forms, for example, cultured cell suspension, protoplasts, leaf sections, cali, etc. A vector can be transferred into plant cells by a variety of methods well known to those skilled in the art, including the polyethylene glycol method, electroporation method, *Agrobacterium*-mediated method, particle gun method, etc. Regeneration of a plant body from transformed plant cells may be performed by the standard methods known in the art. Once the transformed plant body is generated, it is possible to obtain propagative materials (for example, seeds, tubers, cuttings, etc.) from the plant body and produce the transformed plant of this invention on a large scale.

Furthermore, in this invention, it may also be possible to enhance the plant growth by promoting the expression of DNA isolated by the present inventors. In this case, the DNA is inserted into an appropriate vector, and the resulting recombinant vector is transferred into plant cells so as to regenerate the transformed plant cells thus obtained. Vectors used for the expression in plant cells, plant cells into which vectors are transferred, methods for regenerating plant bodies are similar to those in the case where the above-described antisense DNAs and the like are used.

BEST MODE FOR CARRYING OUT THE INVENTION

Figure 1:
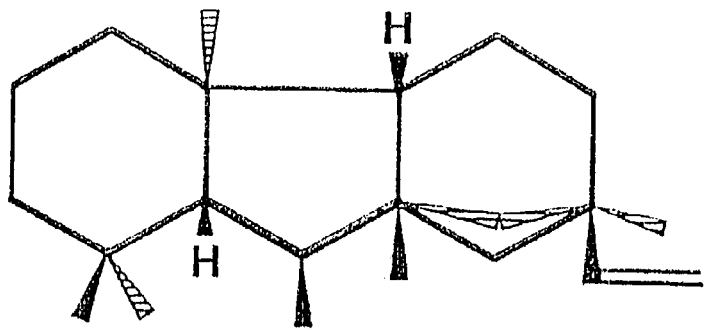
FIG. 1*a* shows a general structure of gibberellin (ent-gibberellan).
FIG. 1*b* shows a major GA biosynthetic pathway in higher plants. The italicized letters indicate a GA-responsive dwarf mutant that lacks a specific GA biosynthetic pathway: ga1, ga2, ga3, ga5, and ga4 from *Arabidopsis*; an1, d5, d3, and d1 from maize; ls and le from pea; d35 (dx) and d18 (dy) from rice.
Figure 1:
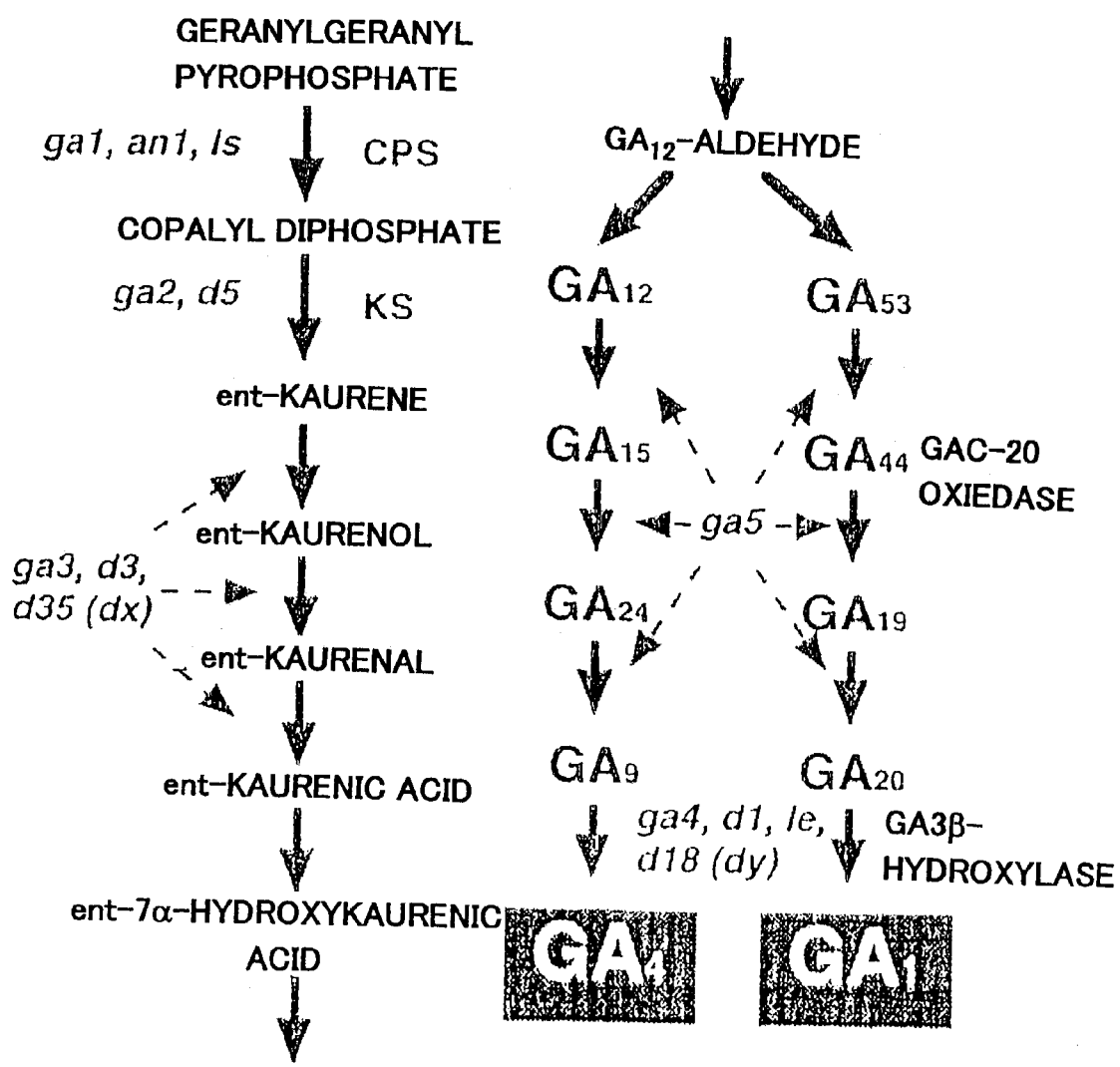
Figure 2:
FIG. 2 is a photograph showing various phenotypes of d18 dwarf plants. From left to right, Taichuu-65 (WT: approximately 1 m at the final stage), Kotake-tamanishiki dwarf (d18$^k$: approximately 65 cm), Waito-C (approximately 55 cm), Hosetsu-waisei dwart (d18$^h$: approximately 15 cm), and Akibare-waisei dwart (Bar=10 cm).
Figure 2:
Figure 2:
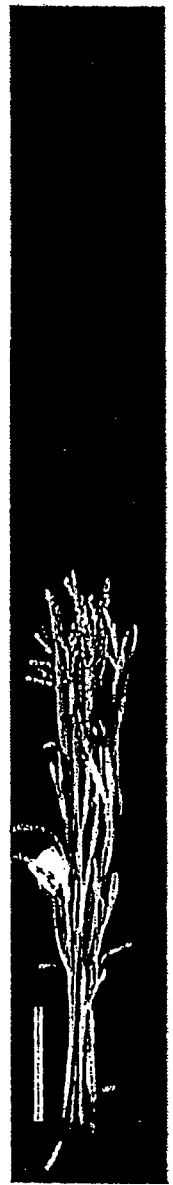
Figure 2:
Figure 2:

The present invention will be explained in detail below with reference to Examples, but is not to be construed as being limited thereto. Rice seeds (*Oryza sativa*, Japonica-type cultivars: "Nipponbare", "Akibare", "Shiokari" and others) were sterilized in 1% NaClO for 1 h and thoroughly rinsed in sterile distilled water and germinated on soil and grown at a greenhouse.

EXAMPLE 1

Isolation of cDNA Clone Encoding GA 3β-hydroxylase

No report on isolation of GA 3β-hydroxylase in monocots is available. Several GA 3β-hydroxylases have been cloned from dicots (Chiang et al., 1995; Martin et al., 1997; Lester et al., 1997).

For the isolation of a partial fragment encoding GA 3β-hydroxylase, PCR was performed using the rice genomic DNA as a template and degenerate primers (5' primer: 5'-GTNGTNAARGTNGGNGARRT-3'/SEQ ID NO: 7; 3' primer: 5'-AYYTARTCRTTGGANGTNAC-3'/SEQ ID NO: 8) designed from the conserved region among the reported dicot's GA 3β-hydroxylase sequences. A 210-bp DNA fragment, which corresponds to the size expected from the reported GA 3β-hydroxylase sequences, was obtained.

To isolate full-length clones, the present inventors screened the rice genomic library with this fragment as a probe. Several clones were isolated and were divided into two groups based on the restriction map of each genomic clone. Finally one clone of each group was entirely sequenced and designated as Os3β-1 and Os3β-2 (Os3β-1 and Os3β-2; *Oriza sativa* GA 3β-hydroxylase -1, -2). Nucleotide sequences of these clones were set forth in SEQ ID NOs: 5 and 6. Os3β-1 shared the sequence with the fragment used as a probe, but Os3β-2 contained a different sequence at the corresponding region from the fragment.

Based on the sequence of each clone, the present inventors performed RT-PCR using the total RNA isolated from seedlings (rice shoot apices) or unopened flowers to obtain cDNA fragment. As a result, full-length cDNA clones encoding GA 3β-hydroxylases were obtained. Each cDNA, Os3β-1 or Os3β-2, contained an open reading frame encoding a polypeptide with 379 or 373 amino acids, respectively. Nucleotide sequences of these clones are set forth in SEQ ID NOs: 3 and 4. The Os3β-2 genomic DNA contained a single short intron (110 bp) and the intron was located at the same position as previously reported GA 3β-hydroxylases in dicot. The genomic DNA of the other clone, Os3β-1, contained two introns. One was located at the same position as the intron of Os3β-2 and its size was comparable to that of Os3β-2 (110 bp). The other was located at the position of the binding site of the co-factor, 2-oxoglutarate (400 bp) (data not shown). The deduced amino acid sequences of both clones shared a high degree of similarity to other GA 3β-hydroxylases, and they showed the highest similarity to each other (56.6% identity, and 88.2% similarity).

Nucleotide sequences were determined by the dideoxynucleotide chain-termination method using an automated sequencing system (ABI373A). Analysis of sequences was carried out using GENETYX computer software (Software Kaihatsu Co., Japan).

EXAMPLE 2

Identification and Characterization of d18 Alleles

Previous quantitative analyses and bioassay of the dwarf rice plants indicated that the D18 gene encodes a GA 3β-hydroxylase. The D18 locus has been identified on chromosome 1, flanking to the FS-2 locus at the bottom of this chromosome. To investigate that the isolated GA 3β-hydroxylase clones correspond to the D18 gene, the present inventors mapped two clones on the rice genome using RFLP (Restriction Fragment Length Polymorphism) analysis.

Figure 3:
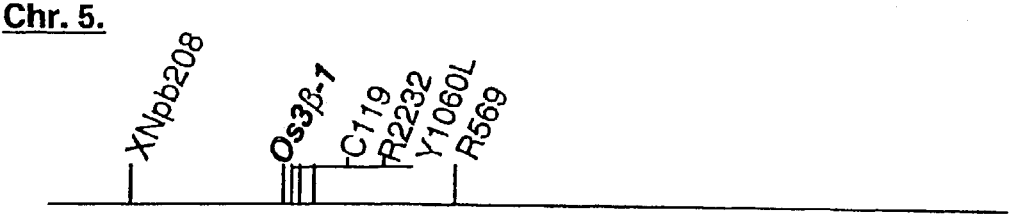
FIG. 3 shows the loci of GA 3β-hydroxylase (Os3β-1 and Os3β-2) genes and various RFLP makers on rice chromosomes 1 and 5.
Figure 3:
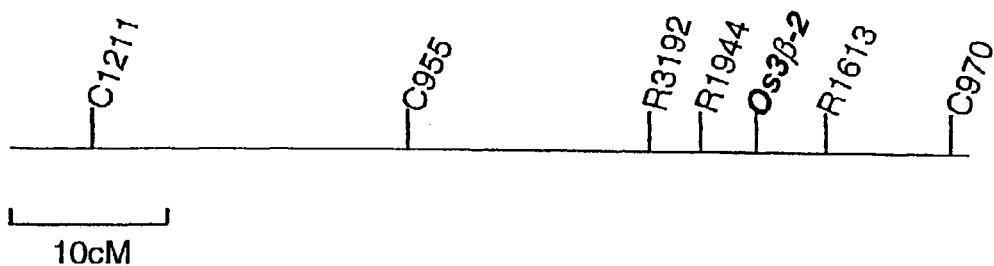

RFLP of Os3β-1 or Os3β-2 were present between Asominori (a Japonica rice) and IR 24 (an Indica rice) DNAs digested with EcoRI or ApaI, respectively. Linkage analysis was performed with digested genomic DNA from F2 progeny of crosses between Asominori and IR 24. Os3β-1 and Os3β-2 are mapped on the top of chromosome 5 and the bottom of chromosome 1, respectively (FIG. 3). This result suggests that the Os3β-2 locus corresponds to the D18 locus.

Further analysis was performed to confirm that Os3β-2 is located at the D18 locus. There are four independent conventional mutants generated by the loss-of-function of the D18 gene. The mutations may be caused by the DNA rearrangements and/or deletions of the D18 gene by mutagenesis using γ-irradiation. Therefore, RFLP at the position of Os3β-2 between a wild type and these mutants may be observed if Os3β-2 is the D18 gene.

DNA gel blot analysis of genomic DNA from a wild type (Shiokari or Akibare) and the d18 alleles (ld18$^k$, ld18$^h$, and d18-AD) was performed. ld18$^k$ and ld18$^h$ are isogenic lines of Shiokari background, and d18-AD was isolated from an Akibare mutant generated by mutagenesis with ethylenimines (EI). For DNA gel blot analysis, rice genomic DNA (1 μg per lane) was digested with restriction enzymes, separated by agarose gel electrophoresis, and transferred to Hybond N+ nylon membrane (Amersham) (Sambrook et al., 1989). Hybridization was performed at 65° C. in 0.25 M Na$_2$HPO$_4$, 1 mM EDTA, and 7% SDS. Filters were washed twice for 15 min at 65° C. in 2×SSC, 0.1% SDS and once in 0.1×SSC, 0.1% SDS at 65° C. for 15 min.

Figure 4:
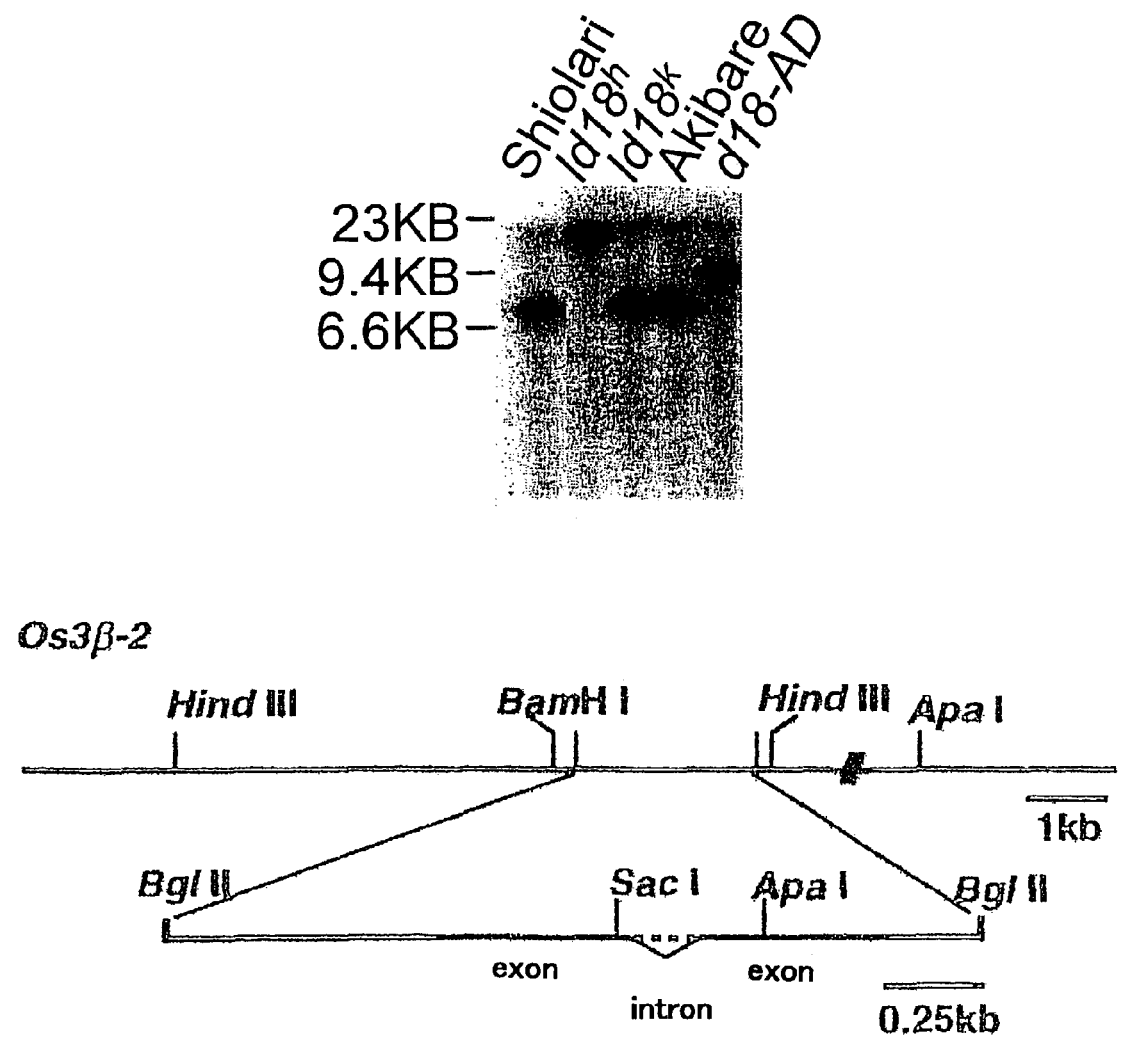
FIG. 4*a* is an electrophoretogram representing the results of RFLP analysis of the D18 and d18 alleles. DNA was isolated from leaf tissues of D18 (Shiokari and Akibare) and d18 allele (d18$^h$, ld18$^h$, and d18-AD) plants. The DNA was digested with ApaI, separated by electrophoresis, bound to nylon filters, and then hybridized. Molecular length markers are given at left in kilobases.
FIG. 4*b* is a restriction map of genomic Os3β-2 clone and its subclone. Genomic clone was obtained by screening the genomic library using the PCR product as a probe. The 2.3-kb BglII fragment subclone contains the entire coding region of D18.

Eight enzymes (BamHI, BglII, ApaI, KpnI, DraI, EcoRV, EcoRI, and HindIII) were used to digest these genomic DNA to find RFLP between the wild type plants and the mutants. Polymorphisms were observed when the DNAs from d18-AD and ld18$^h$ were digested with ApaI, while ld18$^k$ did not show any polymorphisms when digested with any enzymes tested (FIG. 4).

The result of RFLP analysis strongly suggests that d18-AD has a long deletion in the D18 locus, while ld18$^h$ has a short deletion including the ApaI site. To confirm the result, the present inventors analyzed the entire coding sequences of all d18 alleles and compared them with that of the wild type Os3β-2.

Specifically, oligonucleotide primers designed based on the 5' and 3' noncoding sequences of D18 were used to amplify the 1.6-kb fragments containing the entire coding region from D18, d18$^h$, d18k, and d18-w, and then the amplified fragments were sequenced.

As expected, the Os3β-2 coding sequence was altered in all d18 alleles at various positions (Table 1), while the d18-AD produced no RCR product.

TABLE 1

| Allele | Nature of mutation$^a$ | Position in coding sequence | Consequence of mutation |
|---|---|---|---|
| d18-AD (Akibare-waisei) | 7-kb deletion | | absence of a full length of D18 ORF |
| d18$^h$ (Hosetsu-waisei) | GGG to GG, 1-base deletion | Gly$^{251}$ | frameshift, addition of 38 novel amino acids, truncated polypeptide |
| d18k (Kotake-tamanishiki) | CGC to TGC | Arg$^{145}$ | amino acid substitution, substitute Asp to Cys, altered product |
| d18-w (Waito-C) | 9-base deletion | Val$^{57}$ to Arg$^{59}$ | in-frame deletion, absence of a 3-amino-acid residue segment altered product |

$^a$Underlining denotes nucleotide substitution in the d18$^k$ allele.

This supports the above result that d18-AD almost entirely lost the coding sequence (data not shown). In the sequence from ld18$^k$, substitution of C to T at the nucleotide position 433 numbering from the start codon, converted Arginine-168 to Cystine. In d18-w, in-frame deletion of 9 nucleotides at the position of 169 to 177, resulted in deletion of 3 amino acids Valine-57 to Arginine-59. In ld18$^h$, deletion of nucleotide G caused a reading frame shift. These results demonstrate that the Os3β-2 gene is located at the D18 locus, and encodes an GA 3β-hydroxylase.

EXAMPLE 3

Regulation of the Os3β-2 (D18) and Os3β-1 Genes During Plant Growth

To investigate the expression of the D18 and Os3β-1 genes during plant growth, RNA gel blot analysis was performed. For this analysis, total RNA was prepared from various organs or tissues by the standard method (Sambrook et al., 1989). RNA (10 μg per sample) was separated by gel electrophoresis and transferred to a Hybond N+ nylon membrane (Amersham). Hybridization was performed at 65° C. in a solution containing 5×SSC, 10% (w/v) dextran sulfate, 0.5% (w/v) SDS, 0.1 mg/ml denatured salmon sperm DNA. Filters were washed twice for 15 min at 65° C. in 2×SSC, 0.1% SDS and once in 0.1×SSC, 0.1% SDS at 65°

C. for 15 min. A BssHII-PvuII (519 bp) fragment from full-length D18 cDNA and a KpnI-PvuII (310 bp) fragment from Osβ-1, were used as probes.

Figure 5:
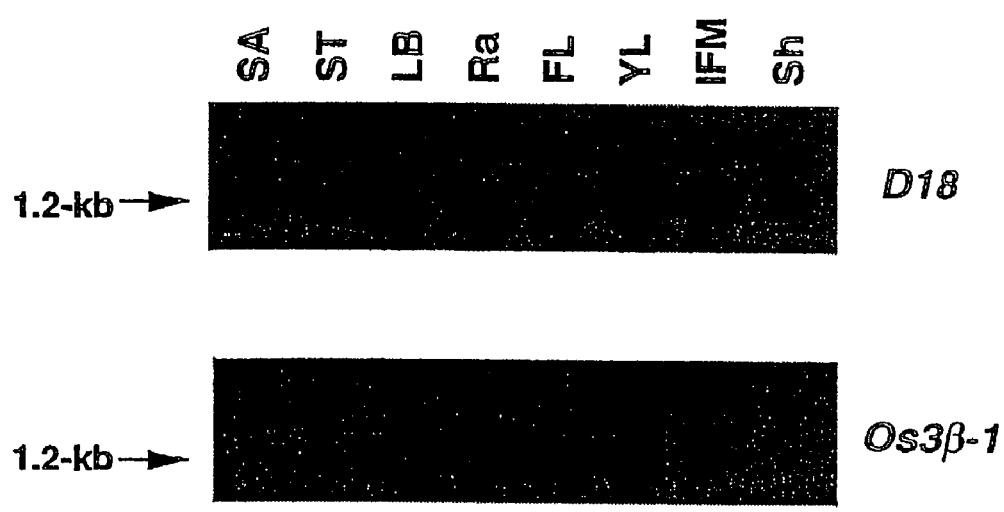
FIG. 5 is an electrophoretogram representing expression patterns of GA 3β-hydroxylases in wild type *Oryza sativa* plants. The patterns were obtained by hybridization of 3β-hydroxylase cDNA D18 and Os3β-1 to northern blots from 10 μg of total RNA extracted from SA (shoot apices), ST (stems), LB (leaf blades), Ra (rachises), FL (flowers), YL (young leaves), IFM (inflorescence meristems), and Sh (2-week-old seedlings).

D18 gene was expressed in every organ tested (FIG. 5). The levels of expression were high in stems, young leaves, and inflorescence meristems, and low in leaf blades and rachises. In contrast, the Os3β-1 mRNA expression was specifically high in the flowers, and low in leaf blades and rachises.

Because D18 and Os3β-1 are highly similar to each other, the present inventors examined the degree of cross-hybridization by genomic southern analysis. When the respective specific probe was used to genomic southern hybridization, cross-hybridization was not detected (data not shown).

EXAMPLE 4

Production of Dwarfed Plant by Suppressing Expression of Os3β-2 (D18) Gene

Figure 7:
FIG. 7 shows the plasmid pBS-SK$^+$ into which the full-length Os3β-2 cDNA has been inserted.
Figure 8:
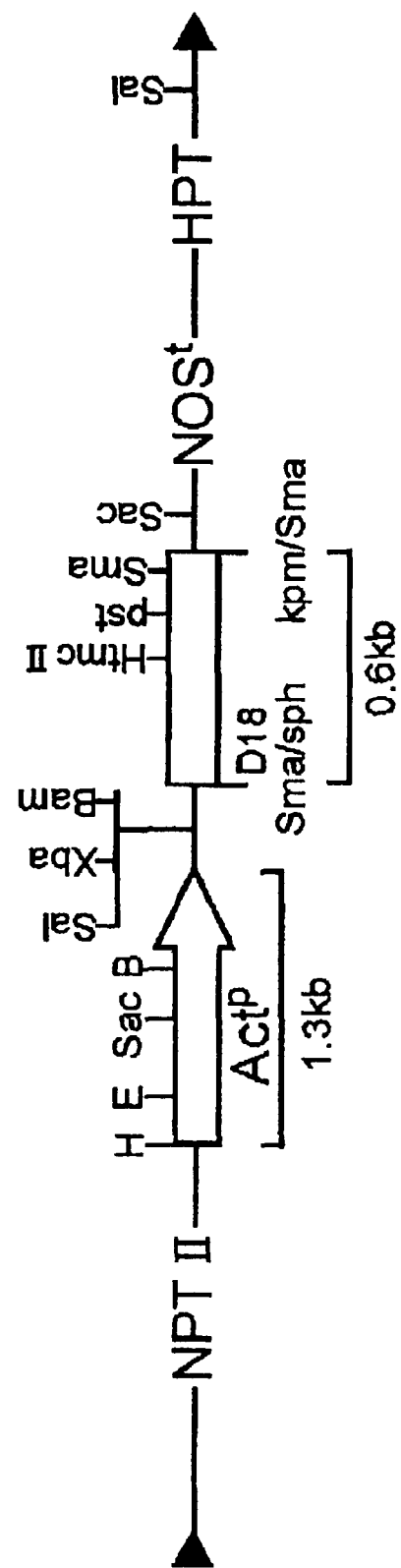
FIG. 8 shows the plasmid pAct-NOS/Hm2 into which the antisense Os3β-2 (D18) gene has been inserted.

A full-length Os3β-2 cDNA that had been cloned to the BamHI-HindIII site in the pBS-SK+ plasmid (FIG. 7), was cleaved out from the vector by the BamHI-HindIII digestion to collect the cDNA, and then its ends were blunted. This blunted full-length cDNA was inserted to the SmaI site of the pAct-NOS/Hm2 plasmid to construct a vector to express the antisense Os3β-2 gene (FIG. 8).

Figure 6:
FIG. 6 is a photograph representing transformed plants in which the Os3β-2 (D18) cDNA is constitutively expressed in the antisense orientation under the control of the actin promoter. A wild type nipponbare plant is on the left, a semi-dwarfed plant on the middle, and a dwarfed plant on the right.

*Agrobacterium* strain EHA101 was transformed with this recombinant plasmid by the electroporation method. Germinating seeds of rice were contacted with the *Agrobacterium* strain and cultured in a selection medium containing kanamycin and hygromycin for 3 weeks to select resistant cells, which were transplanted to a re-differentiation medium so as to obtain dozens of transgenic plants. As a result, plants expressing the antisense Os3β-2 gene became dwarfed compared with the wild type rice plant (FIG. 6).

EXAMPLE 5

Function of Recombinant GA 3β-hydroxylase cDNAs for the predicted protein-coding regions of the Os3β-1 and Os3β-2 genes were each inserted into the pMAL-c2 expression vector (New England Biolabs, Beverly, Mass.) in the sense orientation to obtain a fusion translation product. The constructs thus obtained, pMAL-Os3β-1 and pMAL-Os3β-2, were expressed in *E. coli* strain JM109. Bacterial cells were cultured by shaking in 2×YT medium containing 100 mg/L ampicillin at 37° C. overnight. Then, the culture was diluted 100-fold with a fresh 2×YT medium containing 100 mg/L ampicillin, and further cultured with shaking at 30° C. Four hours later, IPTG was added to the culture to a final concentration of 1 mM, and the mixture was incubated with shaking at 17° C. for further 18 h. After the completion of culturing, the bacterial cells were collected, washed with a washing buffer (containing 50 mM Tris-HCl (pH 8.0), 10% (w/v) glycerol, and 2 mM DTT), suspended in the washing buffer containing lysozyme (1 mg/ml), and allowed to stand for 30 min on ice.

Figure 9:
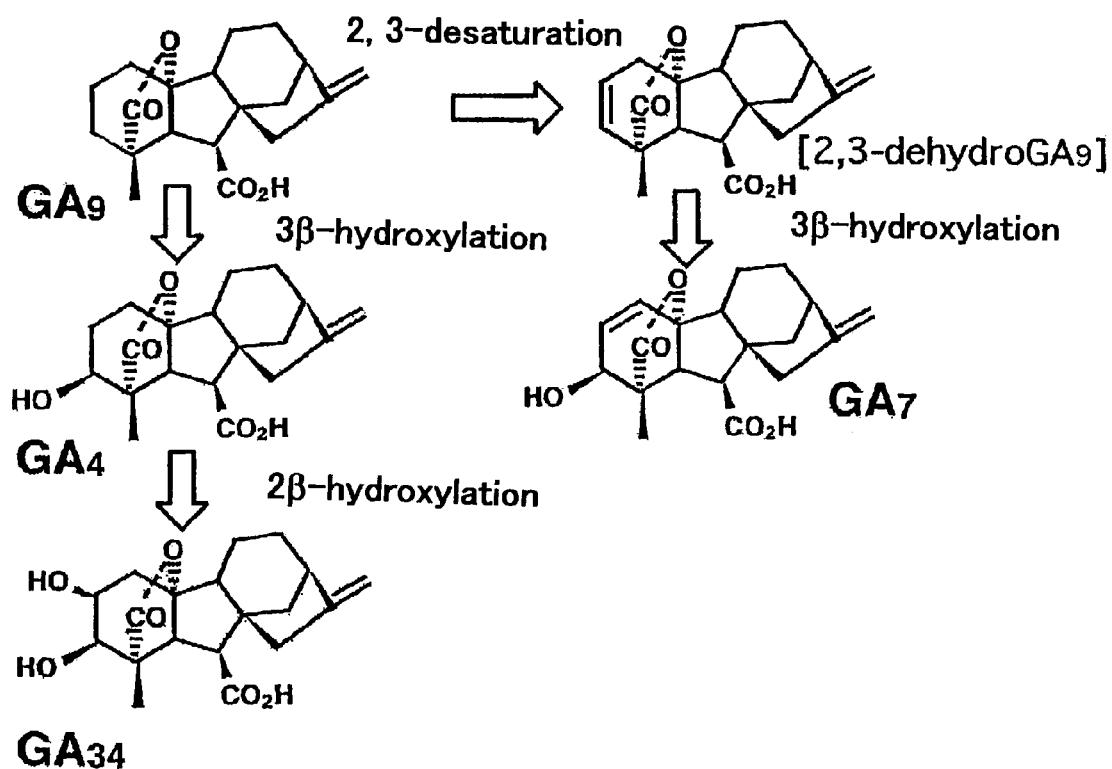
FIG. 9 shows the pathway of the production of $GA_4$, $GA_7$, and $GA_{34}$ catalyzed by an Os3β-1 fusion protein when $GA_9$ is used as a substrate.
Figure 10:
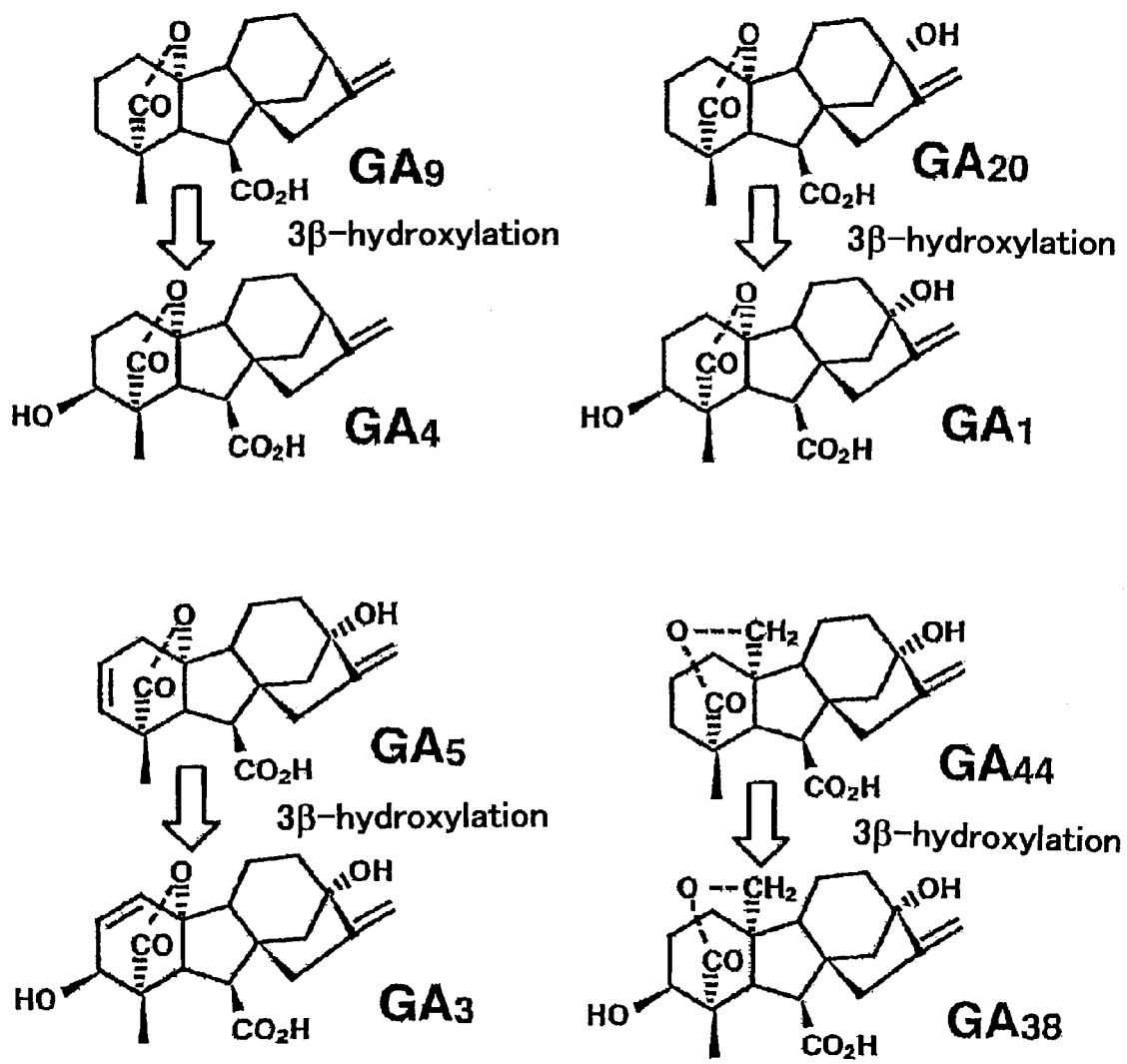
FIG. 10 shows the pathway of the production of 3β-hydroxylated gibberellins ($GA_3$, $GA_4$, $GA_1$, and $GA_{38}$) corresponding to $GA_5$, $GA_9$, $GA_{20}$, and $GA_{44}$, respectively, which are used as substrates, catalyzed by an Os3β-2 fusion protein.

The cell lysate thus obtained was sonicated, centrifuged, and the supernatant was subjected to SDS-PAGE to confirm the expression of the fusion protein. For the assay of enzymatic activity of the Os3β-1 fusion protein, the supernatant was incubated with various gibberellins and cofactors (ascorbate, ferrous iron, and 2-ketoglutarate). For the activity assay of the Os3β-2 fusion protein, the supernatant was purified on a column of amylose resin according to the method described in the manual, and the purified protein thus obtained was similarly incubated as described above. Metabolized gibberellins were identified using GC-MS. In the case of the Os3β-1 fusion protein, the synthesis of $GA_4$ (3β-hydroxylation), $GA_7$ (2,3-unsaturation and 3β-hydroxylation), and $GA_{34}$ (2β-hydroxylation) were confirmed when the substrate was $GA_9$ (FIG. 9), with $GA_4$ and $GA_7$ being dominant among these reaction products. Similar results were obtained when $GA_{20}$ was used as a substrate. Furthermore, when $GA_5$ and $GA_{44}$ were the substrate, only the corresponding 3β-hydroxylated gibberellins ($GA_3$ and $GA_{88}$) were obtained. On the other hand, when $GA_5$, $GA_9$, $GA_{20}$, and $GA_{44}$ were used as the substrate, the Os3β-2 fusion protein produced the corresponding 3β-hydroxylated gibberellins ($GA_3$, $GA_4$, $GA_1$, and $GA_{38}$) (FIG. 10).

The results revealed that the Os3β-1 gene encodes an enzyme catalyzing the nuclear reactions of 2-, 3-unsaturation and 2β-hydroxylation as well as 3β-hydroxylation. Furthermore, it became evident that the Os3β-2 gene encodes an enzyme catalyzing the 3β-hydroxylation.

INDUSTRIAL APPLICABILITY

The present invention has provided novel proteins and genes involved in the activation of plant gibberellins as well as plants whose gibberellin activity has been modified by controlling the expression of these genes. This invention enables modification of gibberellin activation in plants so as to artificially modify the plant types. Suppression of gibberellin activation in plants induces plant dwarf phenotypes due to suppression of longitudinal growth. For example, this could prevent rice plants from bending over when excessive elongation is promoted by ample fertilization. A substantial increase in crops may also be expected due to enhanced efficiency of light reception to leaves. It is also possible to improve efficiency in harvesting and breeding management. Another result of the present invention is to increase the yield of the plant as a whole by elevating the expression of genes of this invention in the plant so as to promote gibberellin activation therein. This strategy is particularly beneficial in improving the yield of feed crops as a whole.

The invention claimed is:

1. An isolated DNA encoding a protein selected from the group consisting of:
   (a) a DNA encoding a protein comprising the amino acid sequence set forth in SEQ ID NO: 2;
   (b) a DNA comprising the nucleotide sequence from position 1 to 1119 set forth in SEQ ID NO 4; and
   (c) a DNA encoding a protein comprising the amino acid sequence set forth in SEQ ID NO:2 in which one to 10 amino acids are substituted, deleted, added, and/or inserted and wherein said protein:
      (i) has gibberellin 3β-hydrolase activity;
      (ii) conserves amino acids corresponding to amino acids from 222 to 229 and 285 to 290 in the amino acid sequence set forth in SEQ ID NO:2; and
      (iii) has a motif represented by Met-Trp-X-Glu-Gly-X-Thr, wherein X is any amino acid.

2. A vector comprising the DNA according to claim 1.

3. A transformed plant cell comprising the DNA according to claim 1 in an expressible state.

4. A transgenic plant comprising the transformed plant cell according to claim 3.

5. A propagative material of the transgenic plant according to claim 4, which propagative material comprises said transformed plant cell.

* * * * *